United States Patent [19]

Danno et al.

[11] Patent Number: 5,209,206
[45] Date of Patent: May 11, 1993

[54] AIR-FUEL RATIO CONTROL SYSTEM

[75] Inventors: Yoshiaki Danno; Tetsurou Ishida; Yoshiaki Kodama, all of Kyoto, Japan

[73] Assignee: Mitsubishi Jidosha Kogyo Kabushiki Kaisha, Tokyo, Japan

[21] Appl. No.: 727,855

[22] Filed: Jul. 10, 1991

[30] Foreign Application Priority Data

Jul. 10, 1990 [JP] Japan .................................. 2-182137
Jul. 17, 1990 [JP] Japan .................................. 2-189227

[51] Int. Cl.$^5$ ........................................... F02M 51/00
[52] U.S. Cl. ..................................... 123/479; 123/672
[58] Field of Search ............................... 123/479, 672; 364/431.07

[56] References Cited

U.S. PATENT DOCUMENTS 4,938,194  7/1990  Kato et al. ........................... 123/479
4,951,632  8/1990  Yakuwa et al. ...................... 123/479
4,980,834 12/1990 Ikada et al. ..................... 364/431.05
5,020,499  6/1991  Kojima et al. ....................... 123/479

Primary Examiner—Raymond A. Nelli

[57] ABSTRACT

An air-fuel ratio control system compares an air-fuel ratio indicated by air-fuel ratio information from an air-fuel ratio sensor and a target air-fuel ratio determined depending on operating conditions of a motor vehicle which incorporates the air-fuel ratio control system, for reliably determining at least a failure of the air-fuel ratio sensor. When a failure of the air-fuel ratio sensor is detected, an air-fuel ratio feedback control process is stopped or the air-fuel ratio sensor is disabled, preventing the air-fuel ratio from being corrected in error based on an output signal from the air-fuel ratio sensor which has failed. Therefore, the air-fuel ratio control system prevents problems such as poor exhaust gas purification, reduced drivability, and unstable engine idling from taking place.

11 Claims, 18 Drawing Sheets

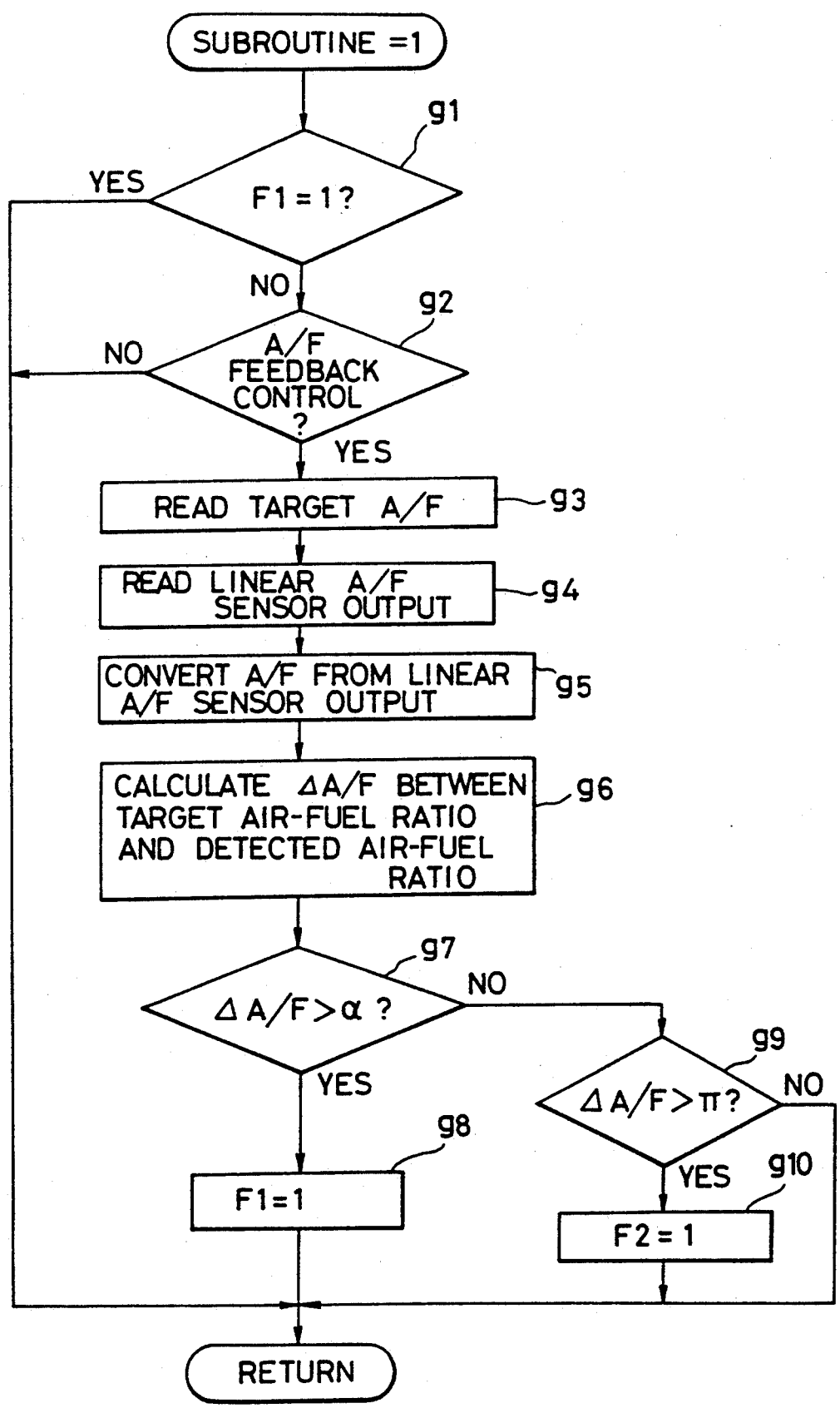

AIR-FUEL RATIO CONTROL SYSTEM

BACKGROUND OF THE INVENTION

1. Field of the Invention

The present invention relates to an air-fuel ratio control system for controlling the air-fuel ratio (A/F) of an air-fuel mixture to be supplied to an internal combustion engine.

2. Related Art

There has been proposed a linear A/F sensor utilizing the oxygen concentration cell capability and oxygen ion pumping capability of zirconia, for detecting whether the air-fuel ratio is on a leaner or richer side of a stoichiometric ratio and also for detecting the value of the air-fuel ratio (see Japanese Laid-Open Patent Publication No. 63(1988)-36140).

One conventional linear A/F sensor will be described below with reference to FIGS. 17 through 20 of the accompanying drawings. FIG. 17 shows a linear A/F sensor including a sensor cell 20 and a pump cell 21 which are shown detached from each other, and each comprise a stabilized zirconia device. The sensor cell 20 and the pump cell 21 are coupled to each other through an insulation layer 22. The sensor cell 20 and the pump cell 21 have respective diffusion holes 23 and 24 defined therein for passing therethrough exhaust gases from an internal combustion engine. The insulation layer 22 has a detecting cavity 25 defined therein into which exhaust gases, can be introduced through the diffusion holes 23 and 24 by the sensor cell 20 and the pump cell 21. The diffusion holes 23 and 24 and the detecting cavity 25 jointly serve as an element for controlling the speed at which the exhaust gases are diffused. The insulation layer 22 also has a reference chamber 25a positioned below the detecting cavity 25 in spaced-apart relation thereto, where the reference chamber 25a is defined between the sensor cell 20 and the pump cell 21. A reference gas such as atmospheric air is introduced into the reference chamber 25a through a communication hole (not shown). As shown in FIG. 18, the sensor cell 20 has porous electrodes 26, 27 of platinum, and the pump cell 21 has porous electrodes 28 and 29 of platinum, where the electrodes 26, 27, 28 and 29 double as catalysts. The sensor cell 20 has an electric heater 30 for heating itself to a temperature range, e.g., 800°±100° C. in order to keep the sensor cell 20 active.

The sensor cell 20 functions as a conventional $O_2$ sensor for developing an electromotive force if there is an oxygen concentration difference between the electrodes 26 and 27. The pump cell 21 also has the same properties as the sensor cell 20, and serves to pump oxygen from a negative electrode to a positive electrode when an electric current (pump current Ip) is caused to flow between the electrodes 28 and 29.

A control assembly 31 detects an electromotive force Vs developed by the sensor cell 20, and also controls the pump current Ip through a feedback loop in order to keep constant the electromotive force Vs, i.e., in order to keep an oxygen concentration corresponding to a stoichiometric ratio in the cavity 25 or the diffusion holes 23 and 24. Since the pump current Ip continuously varies with respect to the air-fuel ratio, as shown in FIG. 19, the air-fuel ratio can be calculated from the pump current Ip.

More specifically, the control assembly 31 includes a comparator 1 and an integrator amplifier 2 with positive and negative power supplies. The comparator 1 compares the electromotive force Vs and a reference voltage Vref corresponding to the stoichiometric ratio. The output signal from the comparator 1 is integrated by the integrator amplifier 2, whose integral output signal is applied as the pump current Ip to the pump cell 21 through a resistor 5. At this time, a voltage drop across the resistor 5 is detected by a current detector 3 which produces a voltage signal commensurate with the pump current Ip. Therefore, the pump current Ip is detected indirectly by the current detector 3. The output signal of the current detector 3 is applied to an adder 4 which then produces an output signal Vout, in the range of 0 to 5 volts, as representing the air-fuel ratio, according to the following equation:

$$Vout = G \cdot Ip + Vstp,$$

where G is the current-to-voltage conversion gain of a current-to-voltage converter which is composed of the resistor 5 and the current detector 3, and Vstp is a step-up voltage in the range of 0 to 5 volts.

In the conventional system shown in FIG. 18, the voltage drop across the resistor 5 is applied to a current inversion detector 6 to detect the direction in which the pump current flows, thereby producing a stoichiometric air-fuel ratio Vstc (see FIG. 20).

The air-fuel ratio of an internal combustion engine is controlled by a feedback control loop so as to achieve a target air-fuel ratio based on the air-fuel ration information produced by an air-fuel ratio sensor. For example, when the air-fuel ratio is controlled within a narrow range or within a window close to the stoichiometric air-fuel ratio, the three-way catalytic converter in the exhaust system can operate highly efficiently. With a lean-burn engine having a lean-NOx catalytic converter and a three-way catalytic converter in the exhaust system, the air-fuel ratio is controlled by a feedback control loop so as to achieve a target air-fuel ratio, i.e., a certain leaner value, based on the air-fuel ratio information from a linear A/F sensor.

Accurate control of the air-fuel ratio so that it reaches a target value while the internal combustion engine is in operation is very important for improved fuel economy, increased engine output power, a more stable idling engine speed, purified exhaust emission, and improved drivability. It is necessary that the linear A/F sensor which produces the air-fuel ratio information be controlled so as not to be thermally deteriorated and destructed due to blackening.

Air-fuel ratio sensors, particularly a linear A/F sensor, are complex in structure, and should be composed of a heater, a sensor cell, and a pump cell in combination for operation.

If the linear A/F sensor, or its pump cell, in particular, fails to operate, then the air-fuel ratio signal Vout and the stoichiometric ratio signal Vstc tend to deviate from their true values, and the air-fuel ratio information produced by the linear A/F sensor becomes low in reliability.

Therefore, in the event of a failure of the linear A/F sensor, it is desirable that the failure be detected early, the air-fuel ratio feedback control process based on the sensor output be stopped, and another air-fuel ratio control process be carried out instead.

It is also necessary for accurate air-fuel ratio control that the air-fuel ratio information be stably produced at all times by the linear A/F sensor.

The air-fuel ratio signal Vout produced by the linear A/F sensor poses no problem insofar as the sensor operates in a stoichiometric air-fuel mixture atmosphere. However, if the linear A/F sensor operates continuously under a leaner air-fuel mixture atmosphere, then the air fuel ratio signal Vout thereof is liable to vary with time as shown in FIG. 14.

More specifically, if the engine operates continuously with the air-fuel ratio controlled for a certain leaner target air-fuel ratio, the air-fuel ratio signal Vout produced by the linear A/F sensor tends to become lower with time. It is known that when the engine is raced to shift the air-fuel ratio temporarily toward a richer side, the pump current changes its direction in the period ER (FIG. 14), and the air-fuel ratio then regains the same value as that at the starting time ST, i.e., the $O_2$ detecting characteristics are regarded as being recovered, at the end of the period ER.

At the time the output signal from the linear A/F sensor indicates some trouble, therefore, the air-fuel ratio information produced thereby becomes less reliable.

In the event of a failure of the linear A/F sensor, therefore, it is desirable to determine whether the sensor is being subjected to a malfunction from which it can be recovered, or a failure from which it cannot be recovered, so that any subsequent air-fuel ratio feedback control process may be interrupted or another air-fuel ratio feedback control process may be selected instead of the feedback control process.

SUMMARY OF THE INVENTION

It is an object of the present invention to provide an air-fuel ratio control system which is capable of reliably determining at least a failure from which an air-fuel ratio sensor cannot be recovered, and of subsequently carrying out a suitable process depending on the failure, for thereby preventing various problems such as poor exhaust gas purification, a reduction in drivability, and unstable engine idling.

According to the present invention, there is provided an air-fuel ratio control system for an internal combustion engine on a motor vehicle, comprising an air-fuel ratio sensor for producing an air-fuel ratio signal indicative of the concentration of oxygen in an exhaust gas produced by a burned air-fuel mixture in the internal combustion engine, and failure determining means responsive to an output signal from said air-fuel ratio sensor and a target air-fuel ratio determined depending on operating conditions of the motor vehicle, for determining at least an irreparable failure of said air-fuel ratio sensor through comparison between said output signal and said target air-fuel ratio.

According to the present invention, there is also provided an air-fuel ratio control system for an internal combustion engine on a motor vehicle, comprising an air-fuel ratio sensor for producing an air-fuel ratio signal indicative of the concentration of oxygen in an exhaust gas produced by a burned air-fuel mixture in the internal combustion engine, first means comprising failure determining means responsive to an output signal from said air-fuel ratio sensor and a target air-fuel ratio determined depending on operating conditions of the motor vehicle, for determining at least an irreparable failure of said air-fuel ratio sensor through comparison between said output signal and said target air-fuel ratio, air-fuel ratio feedback control means for correcting an air-fuel ratio correction according to at least said air-fuel ratio signal so that an actual air-fuel ratio of the internal combustion engine is equalized to said target air-fuel ratio, and second means comprising failure processing means for disabling said air-fuel ratio feedback control means and said air-fuel ratio sensor in response to an output signal from said failure determining means which indicates an irreparable failure of said air-fuel ratio sensor.

The air-fuel ratio control system compares an air-fuel ratio indicated by air-fuel ratio information from an air-fuel ratio sensor and a target air-fuel ratio determined depending on operating conditions of a motor vehicle which incorporates the air-fuel ratio control system, for reliably determining at least a failure of the air-fuel ratio sensor. When a failure of the air-fuel ratio sensor is detected, an air-fuel ratio feedback control process is stopped and the air-fuel ratio sensor is disabled, and the air-fuel ratio is prevented from being corrected in error based on an output signal from the air-fuel ratio sensor which has failed.

The air-fuel ratio control system is therefore effective to prevent problems such as poor exhaust gas purification, reduced drivability, and unstable engine idling from taking place.

The above and other objects, features, and advantages of the present invention will become apparent from the following description when taken in conjunction with the accompanying drawings which illustrate preferred embodiments of the present invention by way of example.

BRIEF DESCRIPTION OF THE DRAWINGS

FIGS. 15(c) and 16 are flowcharts of subroutines of the control program for controlling an air-fuel ratio;

DETAILED DESCRIPTION OF THE PREFERRED EMBODIMENTS

Figure 1:
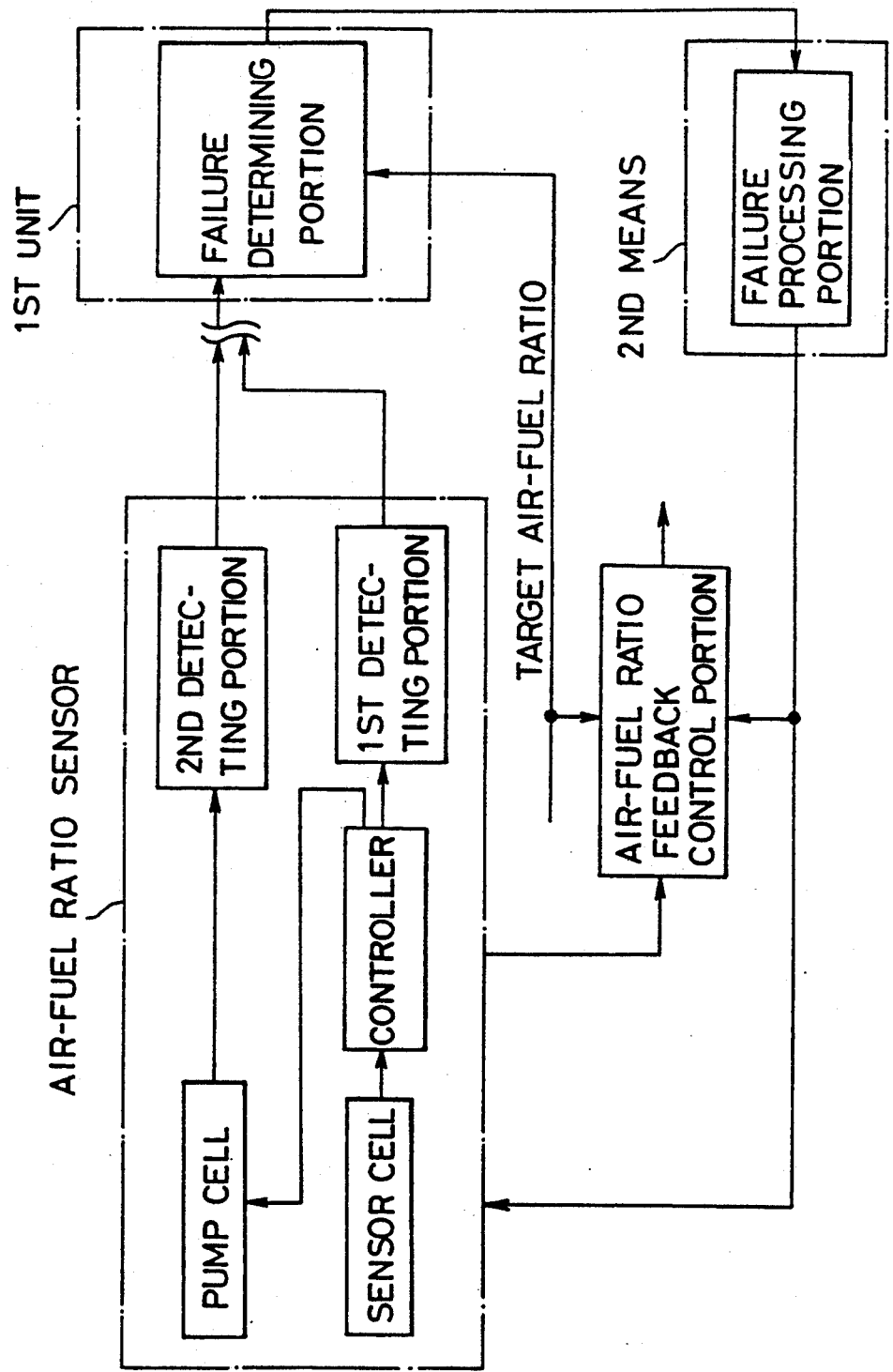
FIG. 1 is a schematic block diagram of an air-fuel ratio control system according to an embodiment of the present invention.
Figure 2:
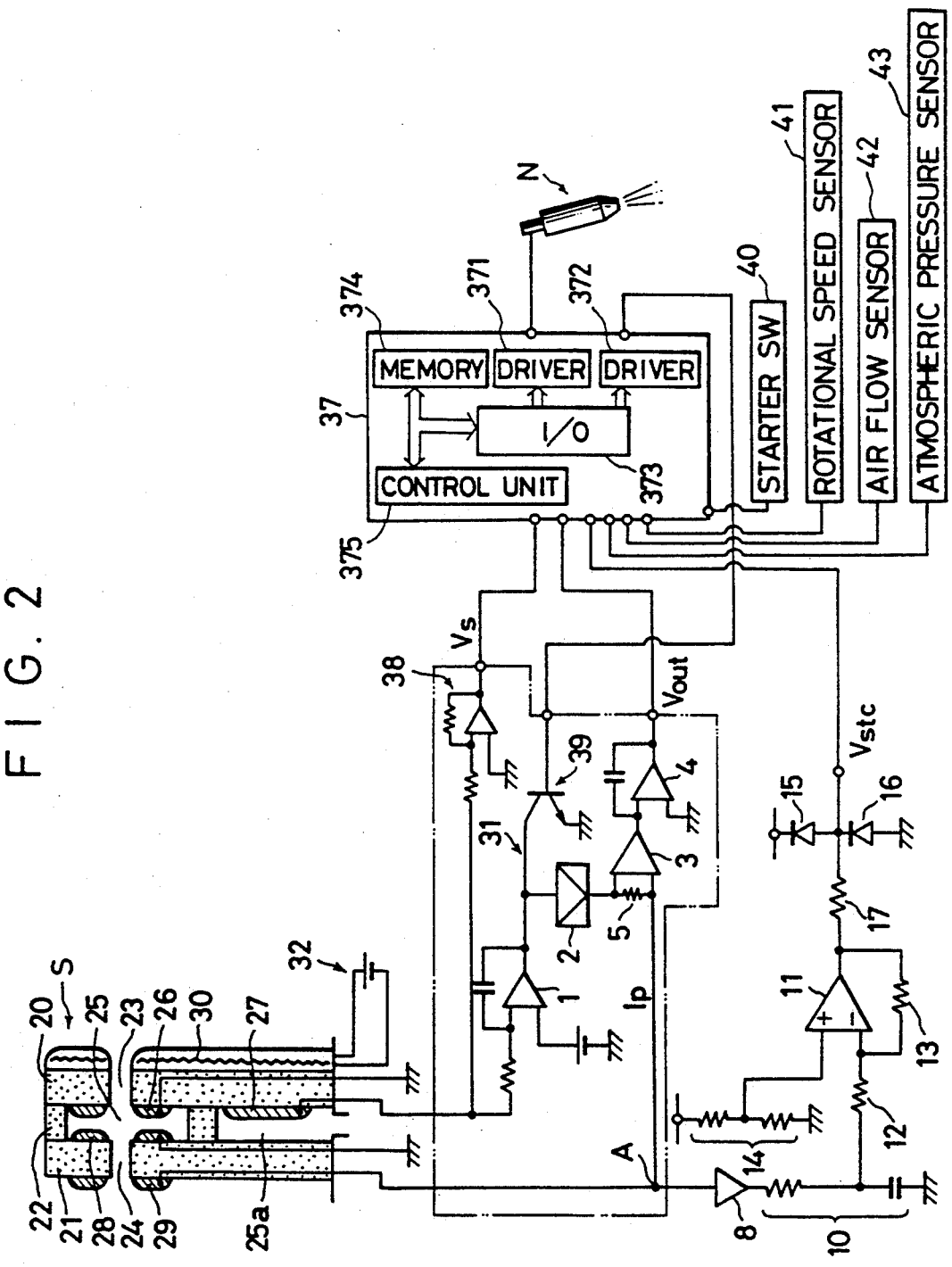
FIG. 2 is a detailed block diagram, partly in cross section, of the air-fuel ratio control system shown in FIG. 1.

FIGS. 1 and 2 show an air-fuel ratio control system according to an embodiment of the present invention.

As shown in FIG. 1, the air-fuel ratio control system generally includes an air-fuel ratio sensor, a first unit including a failure determining portion, and air-fuel ratio feedback control portion, and a second unit including a failure processing portion.

The air-fuel ratio sensor includes a pump cell, a sensor cell, a controller, a first air-fuel ratio detecting portion, and a second air-fuel ratio detecting portion.

As shown in FIG. 2, the air-fuel ratio control system is disposed in a control system for a fuel supply system for an internal combustion engine. The control system for the fuel supply system calculates a rate of fuel to be supplied to the engine based on air-fuel ratio (A/F) information produced by a linear A/F sensor S which is positioned in an exhaust passage of the engine, and the fuel supply system includes a fuel injection nozzle N for injecting the calculated rate of fuel into an intake passage of the engine.

The air-fuel ratio sensor includes the linear A/F sensor S, a control assembly 31 connected as the controller means to the linear A/F sensor, a current detector 3, an adder 4, and a current detecting resistor 5. The air-fuel ratio sensor is of the same arrangement as that of the conventional air-fuel ratio sensor shown in FIG. 18, and will not be described in detail.

In FIG. 2, the control assembly 31 includes a comparator 1 and an integrator amplifier 2 with positive and negative power supplies. The comparator 1 compares an electromotive force Vs generated between the electrodes 26 and 27 of the sensor cell 20 and a reference voltage Vref such as of 0.4 V, for example. The output signal from the comparator 1 is applied to and integrated by the integrator amplifier 2, whose positive or negative control output signal is applied between the electrodes 28 and 29 of the pump cell 21 in order to supply a pump current Ip to the pump cell 21 so that the electromotive force Vs is equalized to the reference voltage Vref (Vs=Vref).

The resistor 5 and the current detector 3 jointly serve as the first air-fuel ratio detecting unit. Specifically, the current detector 3 detects the pump current Ip based on a voltage drop developed across the resistor 5. The pump current IP, which bears air-fuel ratio information, is converted by the adder 4 into an air-fuel ratio signal Vout in the range of 0 to 5 volts. The air-fuel ratio signal Vout is then applied to an engine controller 37.

A pump voltage Vp developed between the electrodes 28 and 29 of the pump cell 21 is detected at a point A by the second air-fuel ratio detecting unit, with the point A being on the line by which the pump current Ip is supplied to the pump, cell 21. The second air-fuel ratio detecting unit includes a buffer amplifier 8 connected to the point A, a CR filter 10, an operational amplifier 11, a resistor 17, and two diodes 15 and 16.

More specifically, the pump voltage Vp is applied through a resistor 12 to the inverting input terminal of the operational amplifier 11, whose output signal is fed back to the inverting input terminal thereof through a resistor 13. An upshifting voltage is applied through a resistive voltage divider 14 to the noninverting input terminal of the operational amplifier 11. The two diodes 15 and 16, which are connected in series to each other, are connected in a reverse-biased manner between a power supply of a predetermined voltage and ground. The junction between the diode 15 and 16 is connected to the output terminal of the operational amplifier 11 through a resistor 17. With this arrangement, the second air-fuel ratio detecting unit serves as an amplifier having a clipping capability. The CR filter 10 serves to prevent a current surge and remove noise.

Figure 3:
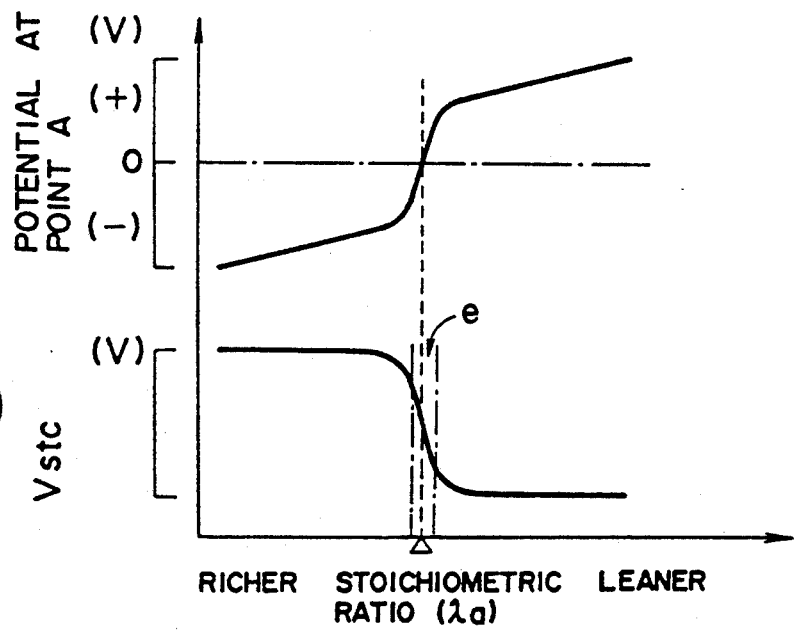
FIGS. 3(a) and 3(b) are diagrams showing a stoichiometric ratio signal Vstc produced in the air-fuel ratio control system shown in FIG. 2.

Basically, the pump voltage Vp has a characteristic curve, as shown in FIG. 3(a), which jumps or increases suddenly at the stoichiometric air-fuel ratio. Since the electromotive force of the pump cell overlaps the, pump voltage Vp, the second air-fuel ratio detecting unit produces, as its output signal, a stoichiometric air-fuel ratio signal Vstc which has different levels on leaner and richer sides of the stoichiometric air-fuel ratio. The stoichiometric air-fuel ratio signal Vstc is applied to the engine controller, 37. Since the second air-fuel ratio detecting unit is mainly composed of the operational amplifier 11, the stoichiometric air-fuel ratio signal Vstc has a relatively smooth waveform as shown in FIG. 3(b). The second air-fuel ratio detecting unit therefore has output characteristics which are similar to those of a stoichiometric air-fuel ratio sensor.

The linear A/F sensor S has an electric heater 30 for heating itself, with the electric heater 30 being connected to a heated driver 32. The heater driver 32 includes a conventional bridge circuit or the like (not shown) for keeping a heater resistance RH at a preset value.

The sensor cell 20 is also connected to a detecting circuit 38 for detecting the electromotive force generated by the sensor cell 20 and producing an output signal Vs corresponding to the detected electromotive force.

A pump current cutting circuit 39 is connected to the input terminal of the integrator amplifier 2 and ground, for example. Thus, in response to a pump current cutting signal from the controller 37, the pump current cutting circuit 39 cuts off the pump current Ip by grounding the input terminal of the integrator amplifier 2.

A starter switch 40 is disposed in a combination switch assembly (not shown) of the engine, and applies an ON or OFF signal to the controller 37.

The controller 37 is mainly composed of a microcomputer, and includes drivers 371 and 372, an input/output interface 373 for receiving various output signals and applying control signals to the drivers 371 and 372, a memory 374 which stores a control program for determining a failure (see FIGS. 4 through 8(a) and 8(b)), a control program for calculating a rate of fuel to be injected (see FIG. 9) and various characteristic data and values, and a control unit 375 for calculating control values according to the control programs.

The functions of the controller 37 will be described below with reference to FIG. 1. The controller 37 has the first unit which includes the failure determining portion, as described above. The failure determining portion receives a signal from at least one of the first air-fuel ratio detecting portion which produces the air-fuel ratio signal Vout depending on the control current from the controller, and the second air-fuel ratio detecting portion which produces the stoichiometric air-fuel ratio signal Vstc in response to the detected control voltage that is applied to the pump cell by the controller. The failure determining portion then compares the received signal with a target air-fuel ratio signal to determine whether the compared signal falls within an allowable range. If the compared signal does not fall within the allowable range, then the failure determining portion determines that the air-fuel ratio sensor has failed.

The controller 37 also has the second unit which includes the failure processing portion, and the air-fuel ratio feedback control portion which effects feedback control on the rate of fuel to be injected based on the air-fuel ratio signal. In response to a failure signal from the first unit, the failure processing portion stops the air-fuel ratio control process which is being carried out by the air-fuel ratio feedback control portion, in cooperation with the pump current cutting circuit 39. As described later on, when the pump current cutting circuit 39 is energized, the air-fuel ratio sensor produces a quasi-signal indicating that the detecting cavity is kept in a stoichiometric air-fuel mixture atmosphere.

A process of determining a failure of the air-fuel ratio sensor and a process of calculating a rate of fuel to be injected into the engine, which are carried out at the same time that the rate of fuel to be injected is controlled under air-fuel ratio feedback control and open-loop control processes by the controller 37, will be described below with reference to the flowcharts of FIGS. 4 through 9.

Figure 5:
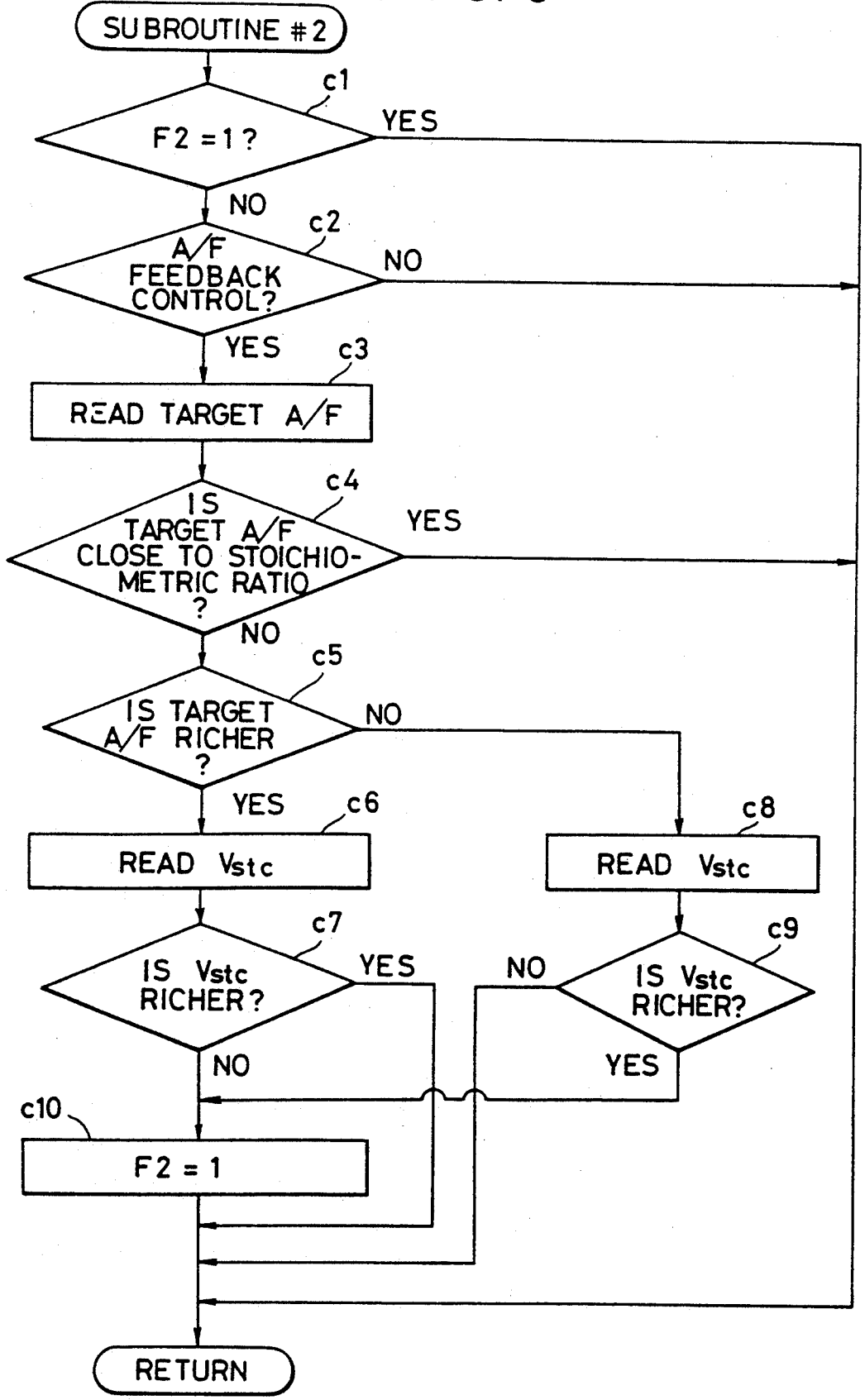
Figure 6:
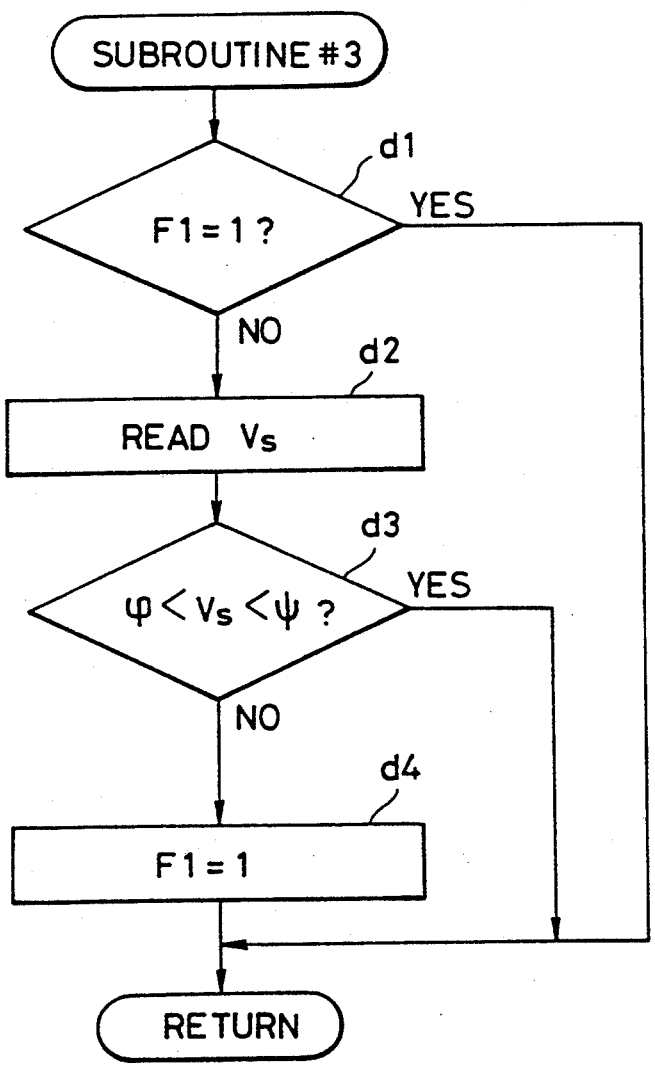
Figure 7:
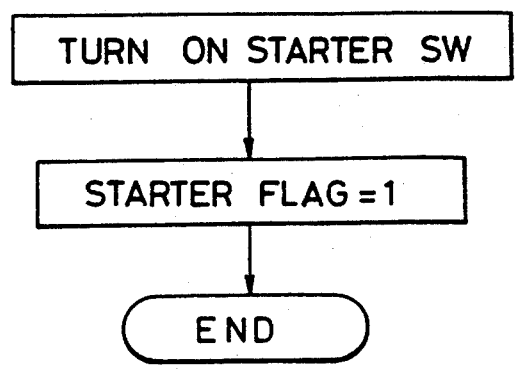
Figure 8A:
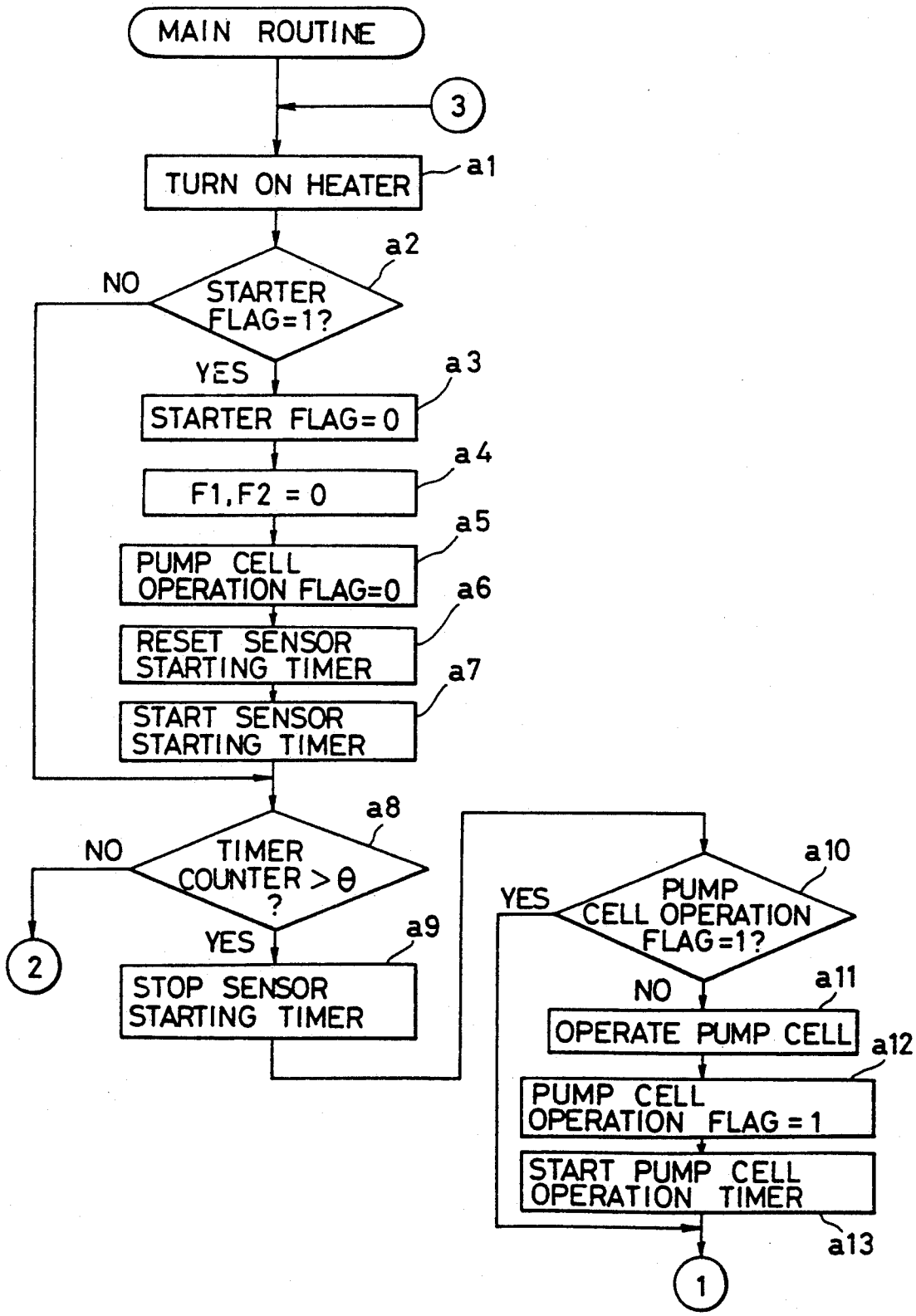
FIGS. 8(a) and 8(b) are a flowchart of a main routine of the control program for determining a failure of an air-fuel ratio sensor, the control program being executed by a controller in the air-fuel ratio control system shown in FIG. 2.
Figure 8B:
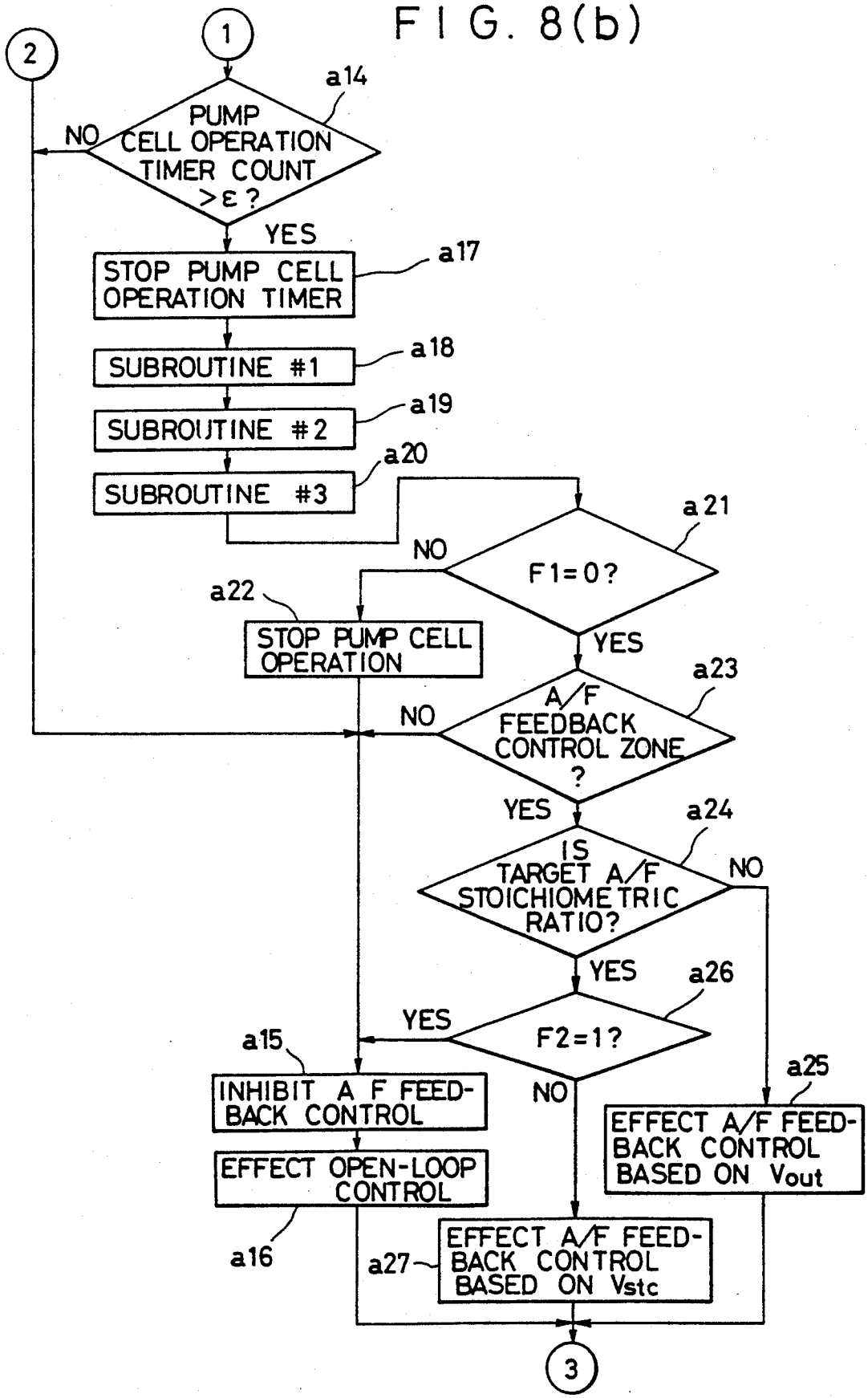

The failure determining process is effected according to the control program shown in FIGS. 4, 5, 6, 7, 8(a) and 8(b). The control program has a main routine shown in FIGS. 8(a) and 8(b). In the main routine, the heater 30 is turned on in a step a1, which is followed by a step a2 that determines whether a starter flag is 1 or not. If the starter flag is not 1, then control jumps to a step a8, and if the starter flag is 1, then control proceeds to a step a3. The starter flag is set when the starter switch SW is turned on, as shown in FIG. 7.

The starter flag is cleared to 0 in the step a3, and fuel determining flags F1 and F2 and a pump cell operation flag that allows the pump current Ip to be supplied are cleared in respective steps a4 and a5. In a step a6, a sensor starting timer is reset which defines a time to start the linear A/F sensor S. Thereafter, the sensor starting timer is started in a step a7. Consequently, the sensor starting timer counts the period of time from the time when the starter switch SW changes from the OFF state to the ON state. A next step a8 determines whether the count of the sensor starting timer exceeds a preset value $\theta$ which has been set to an interval of time long enough for the air-fuel ratio sensor to be activated while the engine is being warmed up. If the count of the sensor starting timer does not exceed the preset value $\theta$, then control goes to a step a15 in which the air-fuel ratio feedback control process is inhibited. Then, the open-loop control process is effected in a step a16, i.e., a rate of fuel to be injected is determined from a predetermined map based on the engine rotational speed and the engine load, and the determined rate of fuel is stored in a predetermined memory area. Thereafter, control goes back from the step a16 to the step a1.

Concurrent with this, a fuel injection routine (not shown) is executed in response to an interrupt at a given crankshaft angle, for thereby injecting fuel to achieve a predetermined target air-fuel ratio.

Thereafter, since the starter flag is 0 in the step a2, control goes from the step a2 directly to the step a8. If the count of the sensor starting timer exceeds the preset value $\theta$ in the step a8, then control proceeds to a step a9. In the step a9, if the sensor starting timer is still in operation, the counting operation thereof is stopped while retaining the count achieved so far. Then, control goes from the step a9 to a step a10.

The step a10 determines whether the pump cell operation flag is 1 or not. If the pump cell operation flag is not 1, then control proceeds to a step a11 in which the pump cell 21 is operated. Then, the pump cell operation flag is set to 1 in a step a12, which is followed by a step a13 in which a pump cell operation timer is started. A step a14 determines whether the count of the pump cell operation timer exceeds a preset value $\epsilon$ which has been set to an interval of time long enough for the output signal of the air-fuel ratio sensor to be stabilized. If the count of the pump cell operation timer does not exceed the preset value $\epsilon$, then control goes to the step a15 for continuing the open-loop control process. If the count of the pump cell operation timer exceeds the preset value $\epsilon$, i.e., if the preset wait time has elapsed and the pump current Ip becomes reliable, then control goes from the step a14 to a step a17. In the step a17, if the pump cell operation timer is still in operation, the counting operation thereof is stopped while retaining the count achieved so far. Then, control goes from the step a17 to a step a18.

The step a18 and subsequent steps a19 and a20 determine whether the linear A/F sensor S has failed or not.

Figure 4:
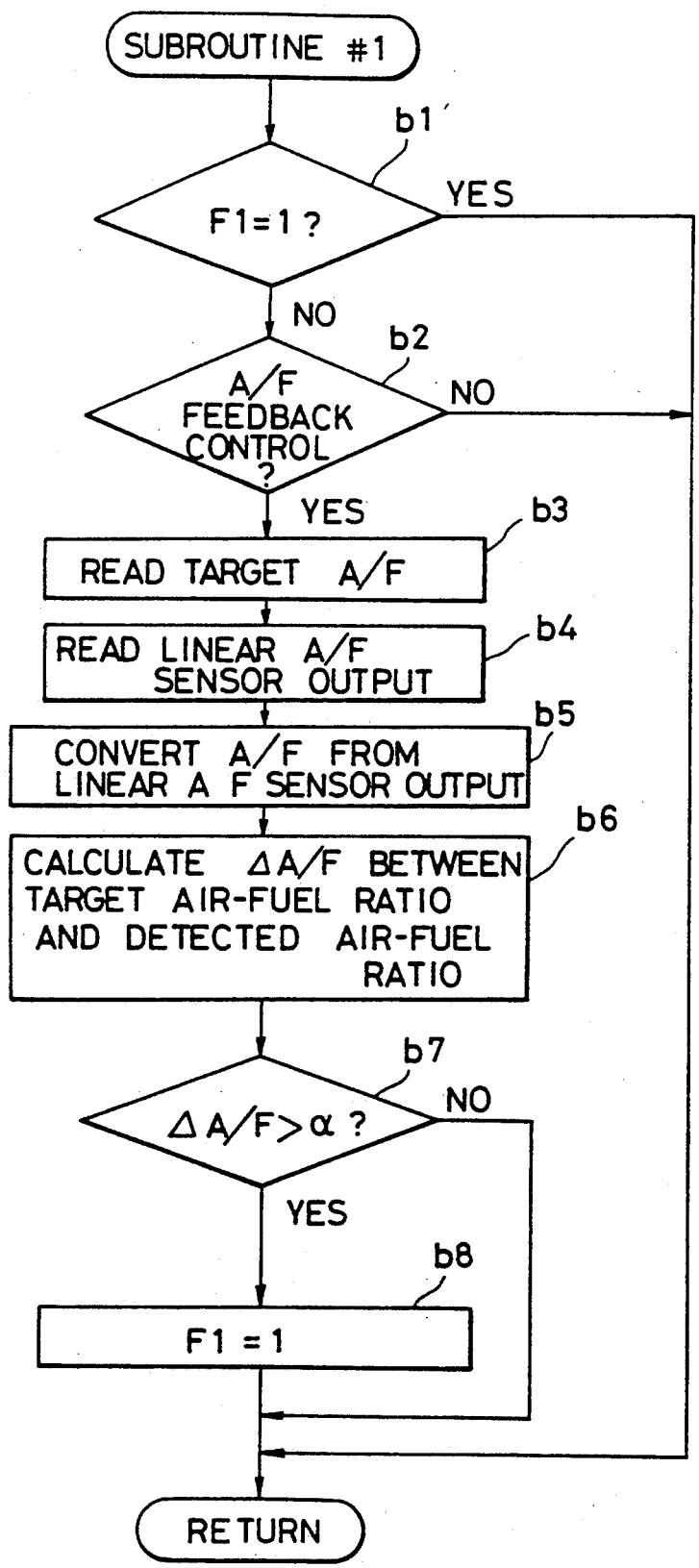
FIGS. 4 through 7 are flowcharts of subroutines of a control program for determining a failure of an air-fuel ratio sensor.

The step a18 is shown as a subroutine #1 in FIG. 4. The subroutine #1 determines whether the linear A/F sensor S has failed or not based on the air-fuel ratio signal Vout. If the fuel determining flag F1 is not 1 in a step b1 and the air-fuel ratio feedback control process is effected in a step b2, then control goes to a step b3. If the fuel determining flag F1 is 1 in the step b1 and the air-fuel ratio feedback control process is not effected in the step b2, then control returns to the main routine shown in FIGS. 8(a) and 8(b).

The step b3 reads a target air-fuel ratio that has already been determined in the main routine depending on operating conditions of the motor vehicle which incorporates the air-fuel ratio control system according to the present embodiment. Then, the air-fuel ratio signal Vout from the linear A/F sensor S is read in a step b4. A step b5 thereafter converts the air-fuel ratio signal Vout into an actual air-fuel ratio according to a predetermined map (not shown) of air-fuel ratios vs. air-fuel ratio signals.

A step b6 calculates a deviation or error $\Delta A/F$ between the target air-fuel ratio and the detected air-fuel ratio from the air-fuel ratio sensor. A step b7 then determines whether the error $\Delta A/F$ exceeds a preset value $\alpha$ for determining a sensor failure or not. If the error $\Delta A/F$ does not exceed the preset value $\alpha$, then control returns to the main routine. If the error $\Delta A/F$ exceeds the preset value $\alpha$, then the fuel determining flag F1 is set to 1 in a step b8. Thereafter, control returns to the main routine.

The step a19 is shown as a subroutine #2 in FIG. 5. The subroutine #2 determines whether the linear A/F sensor S has failed or not based on the stoichiometric air-fuel ratio signal Vstc. If the fuel determining flag F2 is not 1 in a step c1 and the air-fuel ratio feedback control process is effected in a step c2, then control goes to a step c3. If the fuel determining flag F2 is 1 in the step c1 and the air-fuel ratio feedback control process is not effected in the step c2, then control returns to the main routine shown in FIGS. 8(a) and 8(b).

The step c3 reads the target air-fuel ratio that has already been determined in the main routine depending on operating conditions of the motor vehicle. Then, a step c4 determines whether the target air-fuel ratio is close to the stoichiometric air-fuel ratio (i.e., falls in a range indicated by e in FIG. 3). If the target air-fuel ratio is close to the stoichiometric air-fuel ratio, then control returns to the main routine, and if not, then control proceeds to a step c5.

The step c5 determines whether the target air-fuel ratio is richer than the stoichiometric air-fuel ratio. If the target air-fuel ratio is richer than the stoichiometric air-fuel ratio, then control goes to a step c6, and otherwise, control goes to a step c8.

The step c6 reads the present stoichiometric air-fuel ratio signal Vstc, and a subsequent step c7 determines whether the read stoichiometric air-fuel ratio signal Vstc indicates a richer value. If the signal Vstc indicates a richer value in the step c7, then control returns to the main routine. If the stoichiometric air-fuel ratio signal Vstc indicates a leaner value in the step c7, then/since the target air-fuel ratio is richer than the stoichiometric air-fuel ratio, and hence the target and stoichiometric air-fuel ratios do not agree with each other, it is determined that the air-fuel ratio sensor is suffering some failure, and control goes to a step c10 in which the fuel determining flag F2 is set to 1. Thereafter, control returns to the main routine. The step c8 reads the present stoichiometric air-fuel ratio signal Vstc, and a subsequent step c9 determines whether the read stoichiometric air-fuel ratio signal Vstc indicates a richer value. If the signal Vstc indicates a leaner value in the step c9, then control returns to the main routine. If the stoichiometric air-fuel ratio signal Vstc indicates a richer value in the step c9, then, since the target air-fuel ratio is leaner than the stoichiometric air-fuel ratio, and hence the target and stoichiometric air-fuel ratios do not agree with each other, it is determined that the air-fuel ratio sensor is suffering some failure, and control goes to the step c10 in which the fuel determining flag F2 is set to 1. Thereafter, control returns to the main routine.

The step a20 is shown as a subroutine #3 in FIG. 6. The subroutine #3 determines whether the linear A/F sensor S has failed or not based on the electromotive force Vs generated by the sensor cell 20. If the fuel determining flag F1 is not 1 in a step d1, then control goes to a step d2. If the fuel determining flag F1 is 1 in the step d1, then control returns to the main routine shown in FIGS. 8(a) and 8(b)

In the step d2, the electromotive force Vs generated by the sensor cell 20 is detected by the detecting circuit 38. Then, a step d3 determines whether the detected electromotive force Vs, which may be set to 450 mV, for example, falls within an allowable range of from $\phi$ to $\psi$ or not. The allowable range has experimentally been determined in advance. If the electromotive force Vs falls within the allowable range in the step d3, then control returns to the main routine. If the electromotive force Vs falls outside of the allowable range, then it is determined that the sensor cell 20 is being subjected to some failure, and the fuel determining flag F1 is set to 1 in a step d4. Thereafter, control goes back to the main routine.

After the subroutines #1, #2, #3 in the steps a18, a19 and a20, control goes to a step a21 in the main routine. The step a21 determines whether the fuel determining flag F1 is 0 or not. If the fuel determining flag F1 is not 0, then a pump cell operation stop signal is applied through the driver 372 to the pump current cutting circuit 39 to cut off the pump current Ip in a step a22, for thereby preventing the pump cell 21 from being blackened. Then, control proceeds from the step a22 to the step a15 for the air-fuel ratio open-loop control process.

If the fuel determining flag F1 is 0, then control proceeds from the step a21 to a step a23. The step a23 determines whether the present operating conditions of the motor vehicle fall within an air-fuel ratio feedback control range or not. If the present operating conditions are not in the air-fuel ratio feedback control range, then control goes to the step a15 for the air-fuel ratio open-loop control process.

If the present operating conditions of the motor vehicle are in the air-fuel ratio feedback control zone in the step a23, then control goes to a step a24. The step a24 determines whether the target air-fuel ratio in the present operating conditions is the stoichiometric air-fuel ratio or not. If the target air-fuel ratio is the stoichiometric air-fuel ratio, then control goes to a step a26. If the target air-fuel ratio is not the stoichiometric air-fuel ratio, i.e., is on the leaner or richer side of the stoichiometric air-fuel ratio, then control goes to a step a25.

Figure 9:
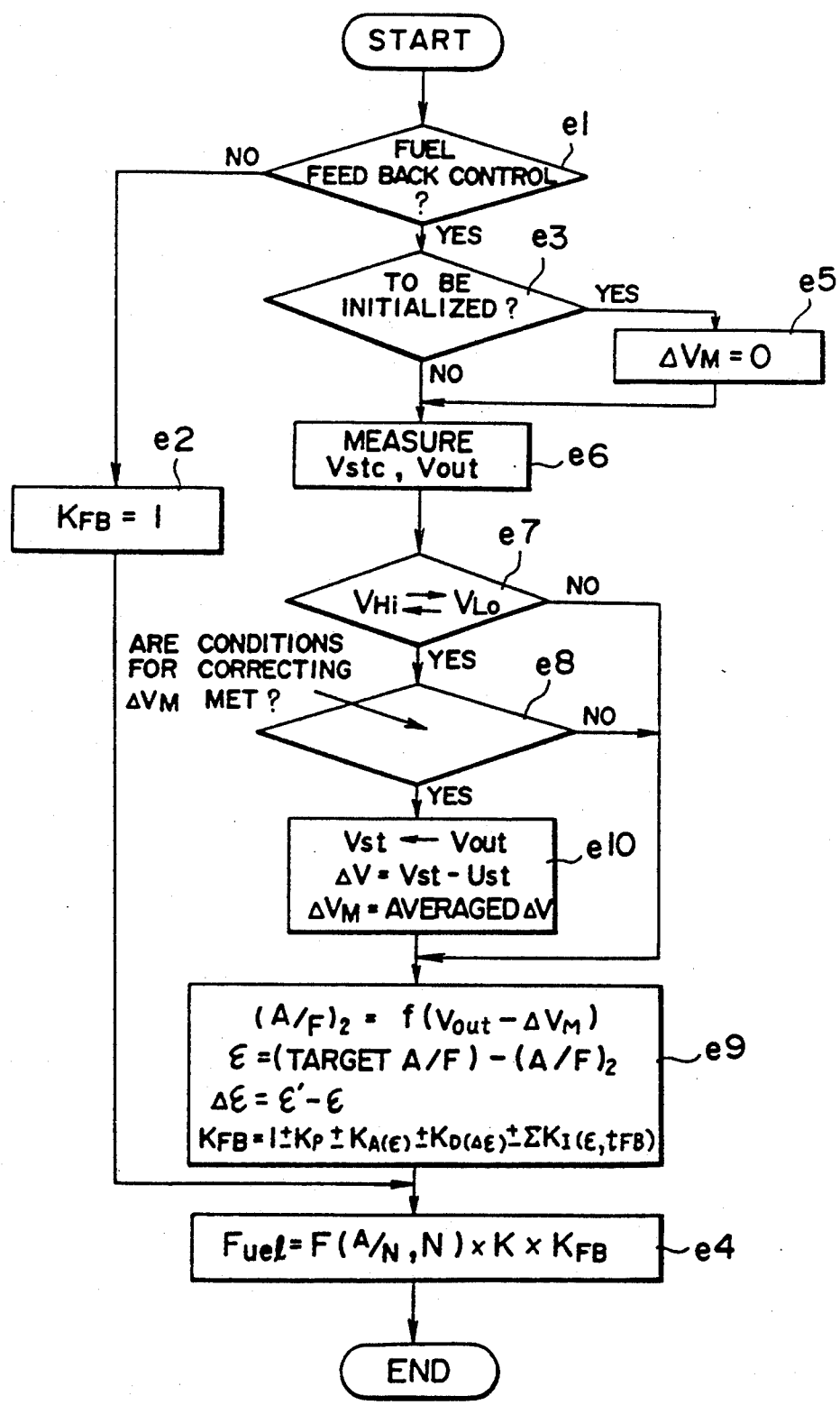
FIG. 9 is a flowchart of a control program for calculating a rate of fuel to be injected, the control programs being also executed by the controller in the air-fuel ratio control system shown in FIG. 2.

The step a26 determines if the fuel determining flag F2 is 1 or not. If the fuel determining flag F2 is not, then control goes to a step a27 in which the a ratio feedback control process is carried out to achieve the operation of the engine at the stoichiometric air-fuel ratio, based on the stoichiometric air-fuel ratio signal Vstc according to a routine for calculating a rate of fuel to be injected as shown in FIG. 9. Thereafter, control goes back to the step a1.

If the fuel determining flag F2 is 1 in the step a26, indicating that the stoichiometric air-fuel ratio signal vstc is abnormal, control goes to the step a15 for the air-fuel ratio open-loop control process.

In the step a25, the air-fuel ratio feedback control process is carried out to achieve the target air-fuel ratio (on the leaner or richer side of the stoichiometric air-fuel ratio), based on the air-fuel ratio signal Vout according to the routine shown in FIG. 9. Thereafter, control returns from the step a25 to the step a1.

The routine shown in FIG. 9 will be described below. First, a step e1 determines whether a condition to start a fuel injection feedback control process is met or not, based on an input signal from a conventional detection.

If the condition is not met, then control goes to a step e2, and if the condition is met, then control goes to a step e3 for the air-fuel ratio feedback control process.

In the step e2, a fuel injection rate corrective coefficient KFs is set to 1. As a result, the engine is continuously operated to equalize the air-fuel ratio to the stoichiometric air-fuel ratio according to the open-loop control process. Then, control proceeds to a step e4 in which a fuel injection rate Fuel is calculated. Specifically, an interrupt routine is effected to read an engine rotational speed N from an engine rotational speed sensor 41, a rate A/N of intake air from the engine rotational sensor 41 and an air flow sensor 42, and atmospheric pressure data from an atmospheric pressure sensor 43. A basic fuel injection rate F(A/N,N) is calculated from the air intake rate A/N and the engine rotational speed N. The calculated basic fuel injection rate F(A/N,N) is multiplied by the corrective coefficient KFB (described later on) and another corrective coefficient K depending on a parameter such as the atmospheric pressure, thus obtaining the fuel injection rate Fuel. Thereafter, control returns from the step e4 to the main routine.

Data, such as the air intake pressure, the throttle opening, or the like, may be employed instead of the intake air rate A/N.

If the condition to start the fuel injection is met in the step e1, then the step e3 determines whether an average value $\Delta V_M$ of errors or differences $\Delta V$ between preset and actual stoichiometric air-fuel ratios is to be cleared or initialized. If the average value $\Delta VM$ is to be cleared, then the averaged value $\Delta V_m$ is cleared in a step e5, which is then followed by a step e6.

The step e6 reads the stoichiometric air-fuel ratio signal Vstc and the air-fuel ratio signal Vout.

Figure 20:
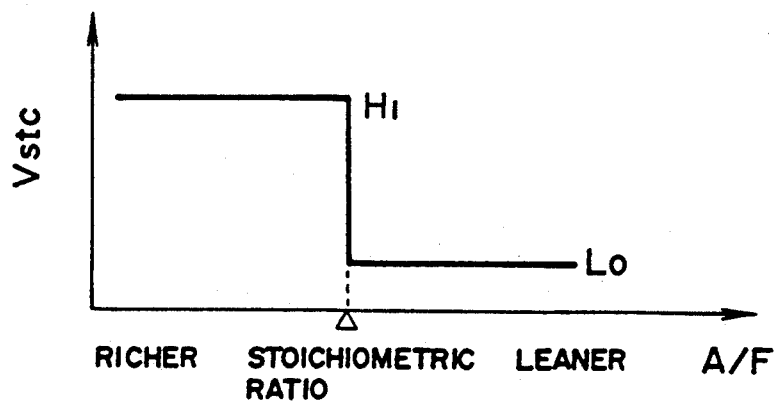
FIG. 20 is a diagram showing a stoichiometric ratio signal with its level depending on the direction of the pump current.

A step e7 compares the read value of Vstc with the value in the previous cycle, and determines whether they differ from each other, i.e., whether the stoichiometric air-fuel ratio signal Vstc has changed between a high level VHi and a low level VLo (see FIG. 20). If the stoichiometric air-fuel ratio signal Vstc has changed in level because the present air-fuel ratio has reached the stoichiometric air-fuel ratio, then control goes to a step e8, and if the stoichiometric air-fuel ratio signal $V_{stc}$ has not changed, then control jumps to a step e9.

The step e8 determines whether conditions for correcting the error average $\Delta V_M$ are satisfied (e.g., if the accelerator or throttle opening has changed by a value less than or equal to a reference value or, if the target air-fuel ratio has been modified immediately before, etc.). If the condition for correcting the error average $\Delta V_M$ are met, then control goes to a step e10, and if the conditions for correcting the error average $\Delta V_M$ are not met, control goes to the step e9.

In the step e10, the air-fuel ratio signal Vout at the time it has reached the stoichiometric air-fuel ratio is stored as an actual value Vst. Then, an error or difference $\Delta V$ is calculated between the actual air-fuel ratio Vst and a predetermined stoichiometric air-fuel ratio Ust, and an average value $\Delta V_M$ of the present and previous errors or differences is calculated in order to eliminate disturbances, so that the average value $\Delta V_M$ is updated.

The step e9 calculates the corrective coefficient $K_{FB}$ for the fuel rate. Specifically, the air-fuel ratio signal Vout at the time is corrected by the error average $\Delta V_M$, thereby producing an air-fuel ratio indicated by $(A/F)_2 = f(Vout - \Delta V_M)$, for example.

Then, the target air-fuel ratio A/F that has already been determined in the main routine depending on operating conditions of the motor vehicle is read, and an error or difference $\epsilon$ between the read target air-fuel ratio A/F and the actual air-fuel ratio $(A/F)_2$ is calculated, and a difference $\Delta \epsilon$ between the presently calculated error $\epsilon$ and the previously calculated error is also calculated. Finally in the step e9, a corrective coefficient $K_{FB}$ is calculated for the control of a fuel injection rate based on the air-fuel ratio.

The corrective coefficient KFs is calculated as the sum of, or difference between, a proportional term $K_A(\epsilon)$ of, a gain depending on the level of the error $\epsilon$, an offset $K_p$ for the prevention of a response delay from the three-way catalytic converter, a differential term $K_{D(\Delta\epsilon)}$ depending on the difference $\Delta\epsilon$, an integral term $\Sigma K_{I(\epsilon,tFB)}$, and 1.

Thereafter, control goes to the step e4 in which a proper rate of fuel to be supplied at the time is calculated from the corrective coefficients $K_{FB}$, K, and the basic fuel injection rate F(A/N,N). Control then returns to the main routine.

The rate of fuel to be supplied which is thus determined in the routine shown in FIG. 9 is called in the fuel injection routine that is executed at the time of an interrupt effected in response to a crankshaft angle signal produced in the main routine. The fuel injection nozzle N is then actuated by the driver 371 for an interval of time corresponding to the determined rate of fuel to be supplied, thereby injecting fuel at the rate which achieved the desired air-fuel ratio.

In the above embodiment, the first and second detecting portion apply the air-fuel ratio signal and the stoichiometric air-fuel ratio signal, respectively, to the controller which has the comparator. However, only one of the air-fuel ratio signal and the stoichiometric air-fuel ratio signal may be applied to the comparator for determining a failure. This alternative results in a simpler system arrangement.

Figure 10:
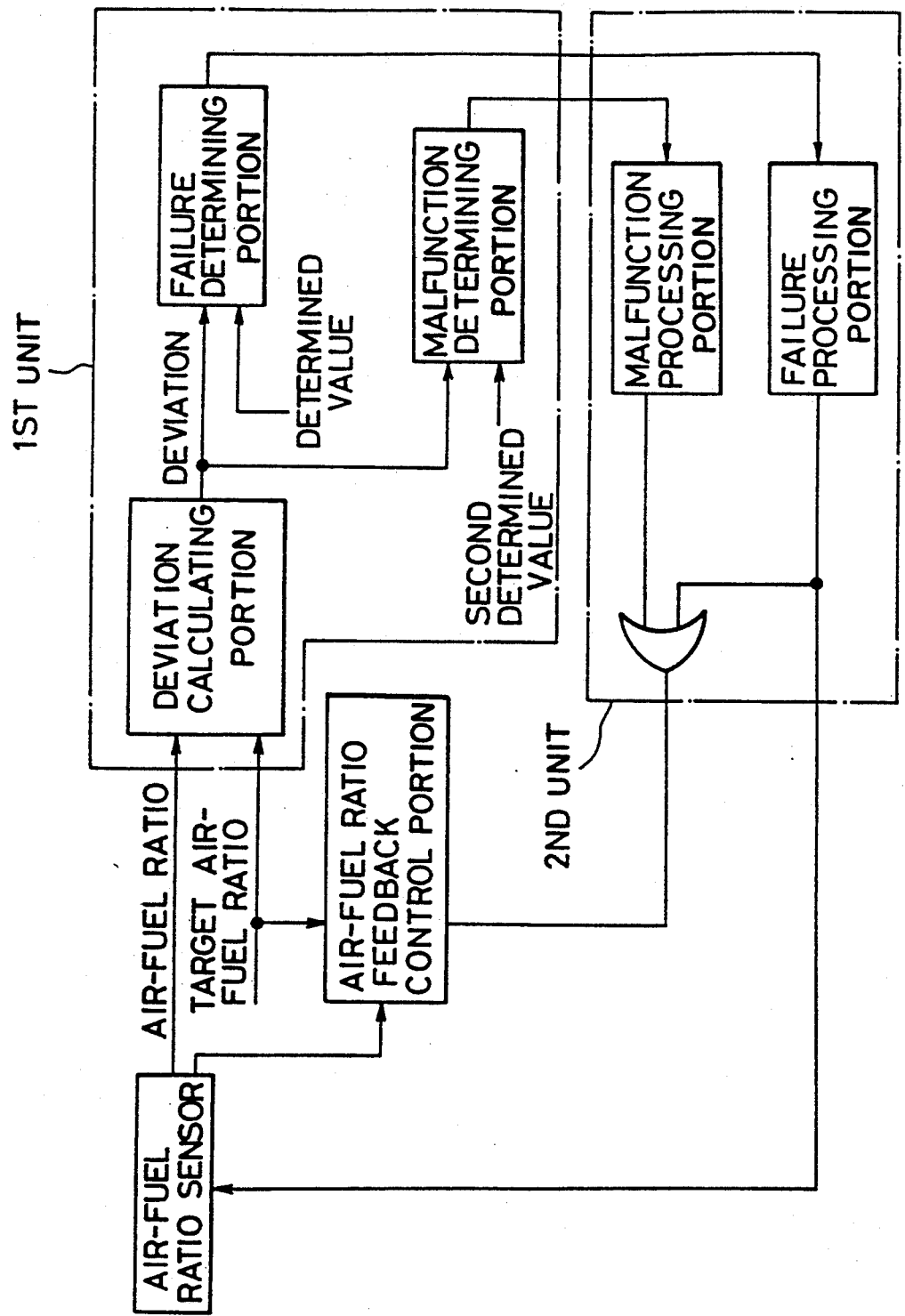
FIG. 10 is a schematic block diagram of an air-fuel ratio control system according to another embodiment of the present invention.
Figure 11:
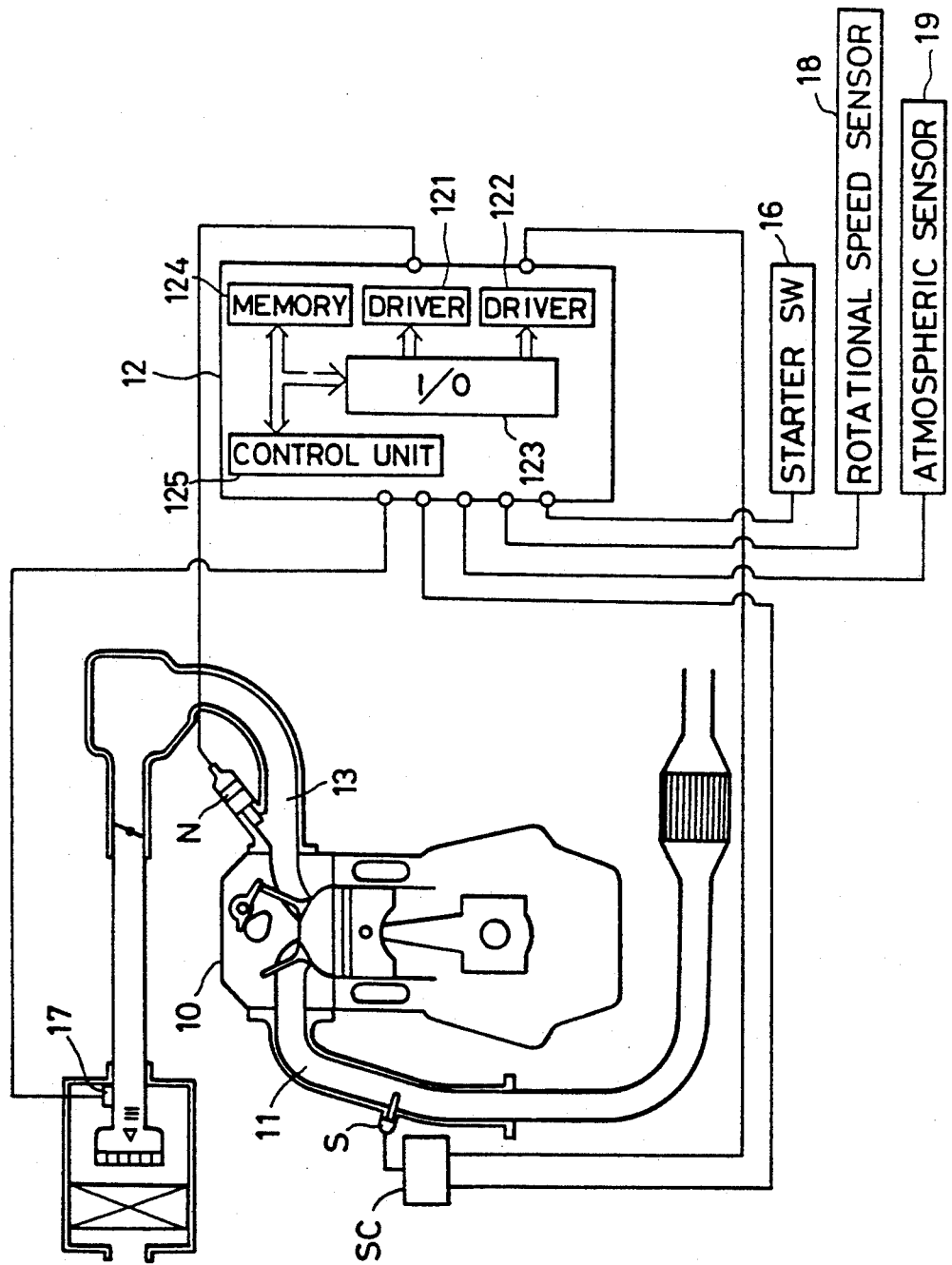
FIG. 11 is a block diagram, partly in cross section, of the air-fuel ratio control system illustrated in FIG. 10.

FIGS. 10 and 11 show an air-fuel ratio control system according to another embodiment of the present invention.

As shown in FIG. 11, the air-fuel ratio control system is disposed in a fuel supply system for an internal combustion engine 10. The fuel supply system calculates a rate of fuel to be supplied to the engine based on air-fuel ratio (A/F) information produced by a linear A/F sensor S which is positioned in an exhaust passage 11 of the engine 10, and includes a fuel injection nozzle N for injecting the calculated rate of fuel into an intake passage 13 of the engine 10.

Figure 18:
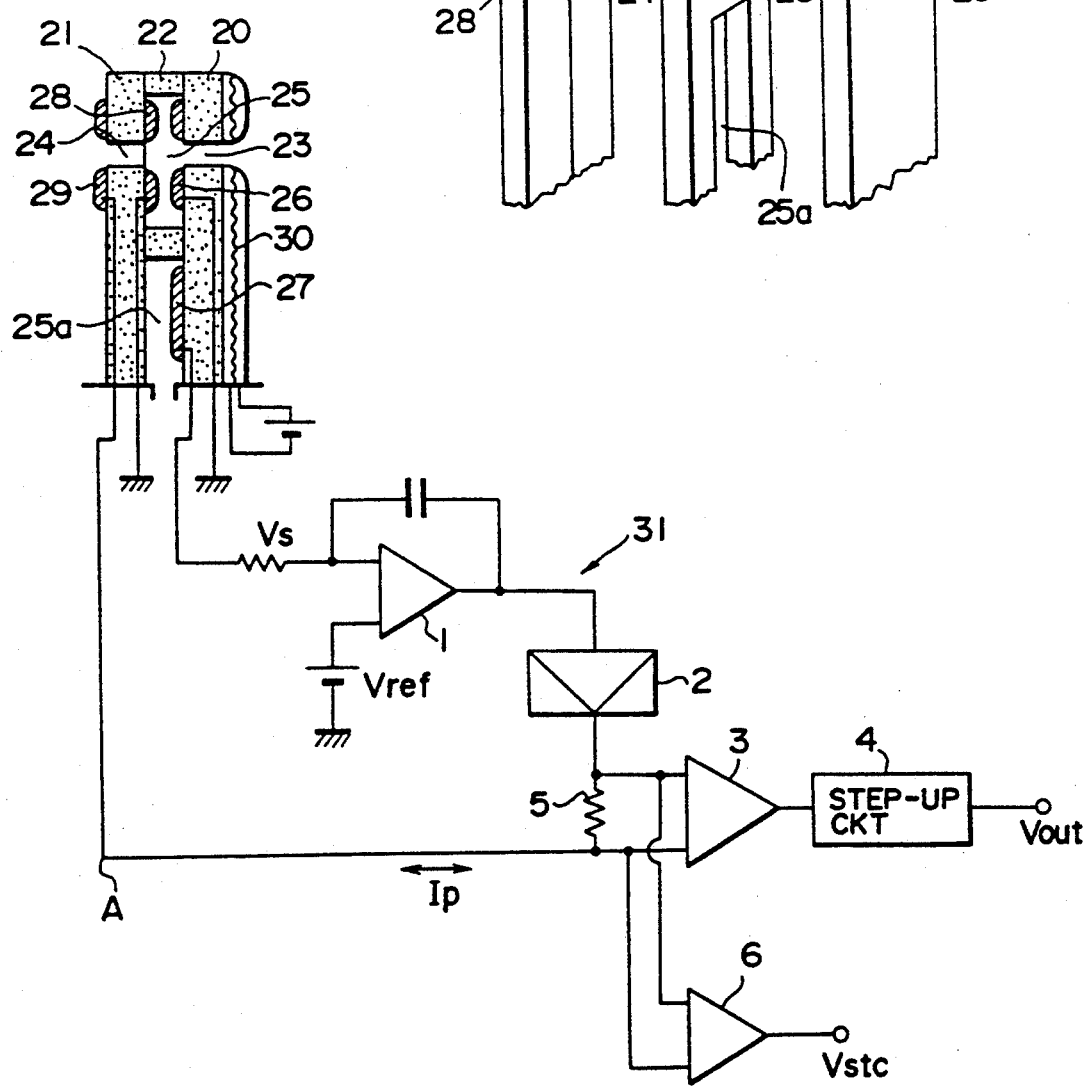
FIG. 18 is a schematic view, partly in block form, of the conventional air-fuel ratio sensor shown in FIG. 17.
Figure 19:
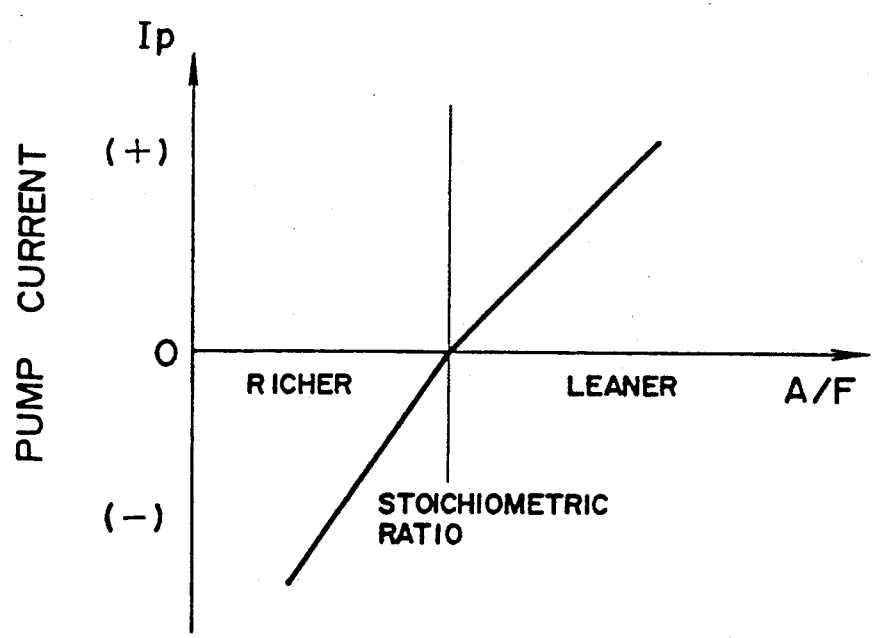
FIG. 19 is a diagram showing the relationship between a pump current and an air-fuel ratio.

The linear A/F sensor S and the control assembly 31 therefor shown in FIG. 11 are of the same arrangement as those of the conventional system shown in FIG. 18, and will not be described in detail.

In FIG. 11, the linear A/F sensor S applies an air-fuel ratio signal Vout, in the range of 0 to 5 volts, to an engine controller 12. The control assembly 31 for the linear A/F sensor S has a pump current cutting circuit 14 connected as shown in FIG. 12, with the pump current cutting circuit 14 serving as part of a failure processing portion.

Figure 12:
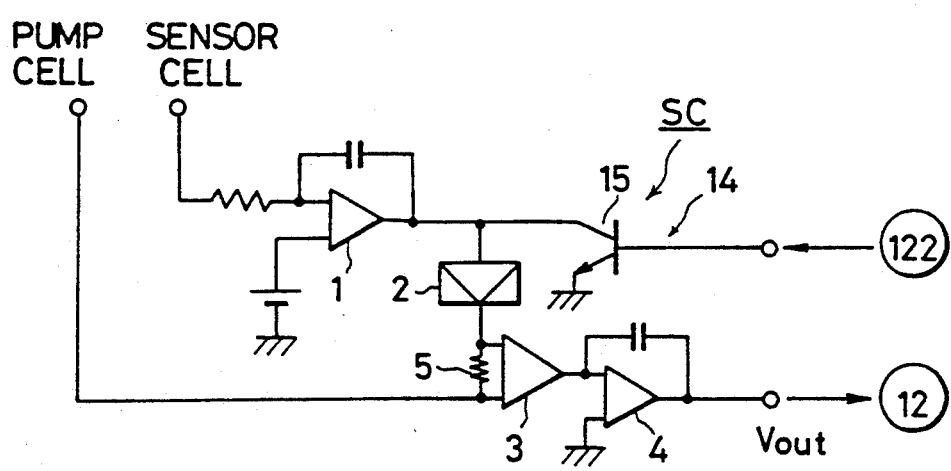
FIG. 12 is a circuit diagram of a sensor driving circuit in the air-fuel ratio control system shown in FIG. 11.

As shown in FIG. 12, the pump current cutting circuit 14 includes a transistor 15 whose base can be supplied with a pump current cutting signal from the controller 12. When the pump current cutting signal is applied to the base of the transistor 15, the junction between a comparator 1 and an integrator amplifier 2 with positive and negative power supplies is brought to a potential of 0. Therefore, a pump current Ip becomes zero, so that the comparator 1 produces an output signal as if the stoichiometric air-fuel ratio were detected.

A starter switch 16 is disposed in a combination switch assembly (not shown) of the engine, and applies an ON or OFF signal to the controller 12 as shown in FIG. 11. An air flow sensor 17 applies a signal indicative of intake air rate information to the controller 12. An engine rotational speed sensor 18 applies a signal indicative of engine rotational speed information to the controller 12. An atmospheric pressure sensor 19 applies a signal indicative of atmospheric pressure information to the controller 12.

Figure 15C:
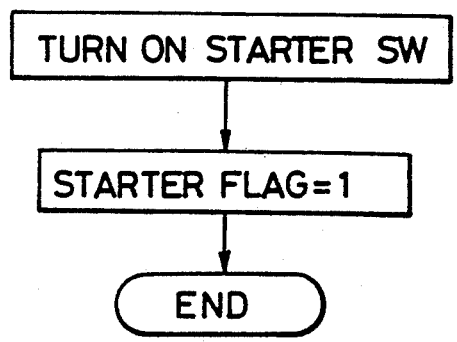
Figure 15A:
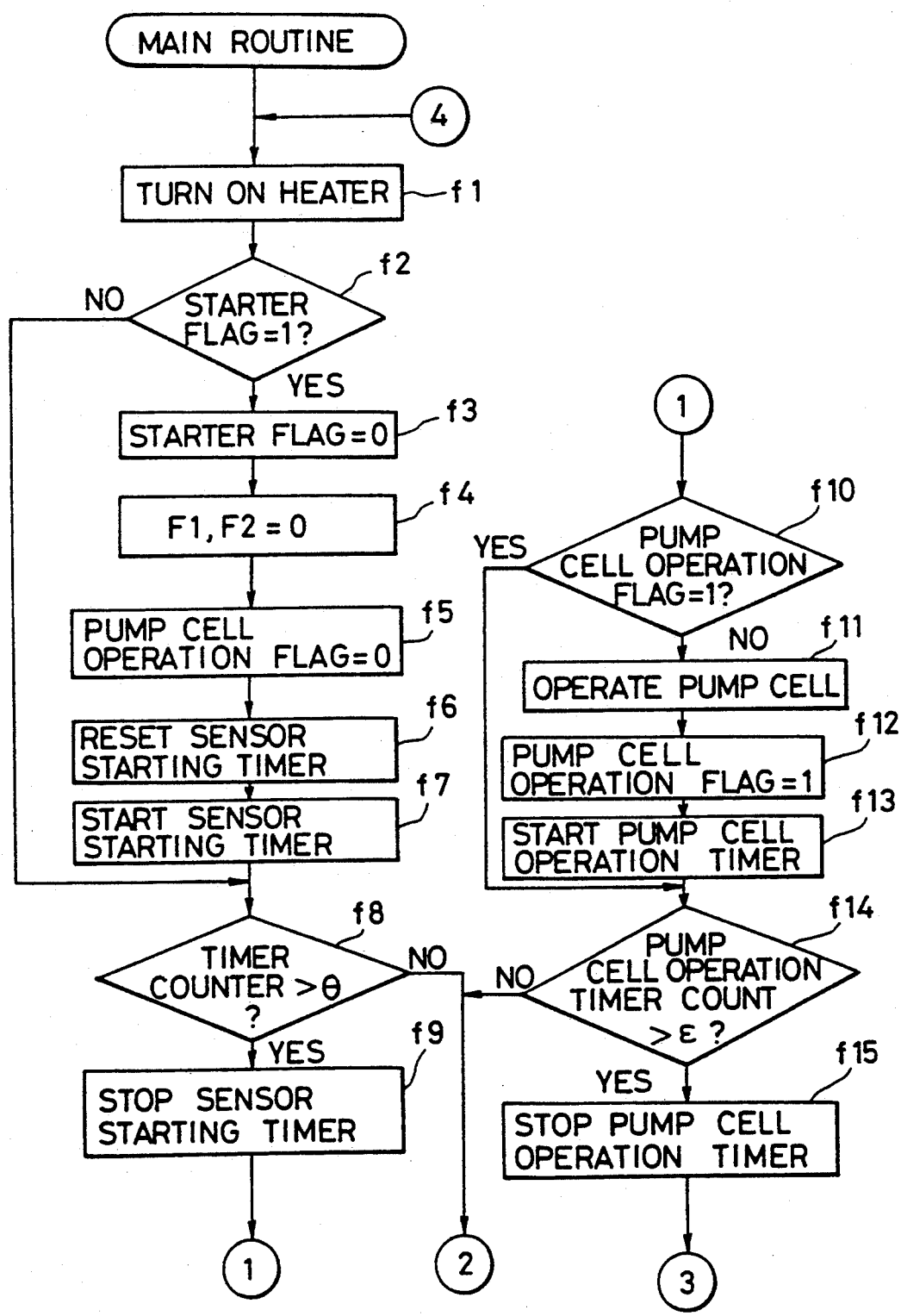
FIGS. 15(a) and 15(b) are flowcharts of a main routine of a control program for controlling an air-fuel ratio, the control program being executed by a controller in the air-fuel ratio control system shown in FIG. 11.
Figure 15B:
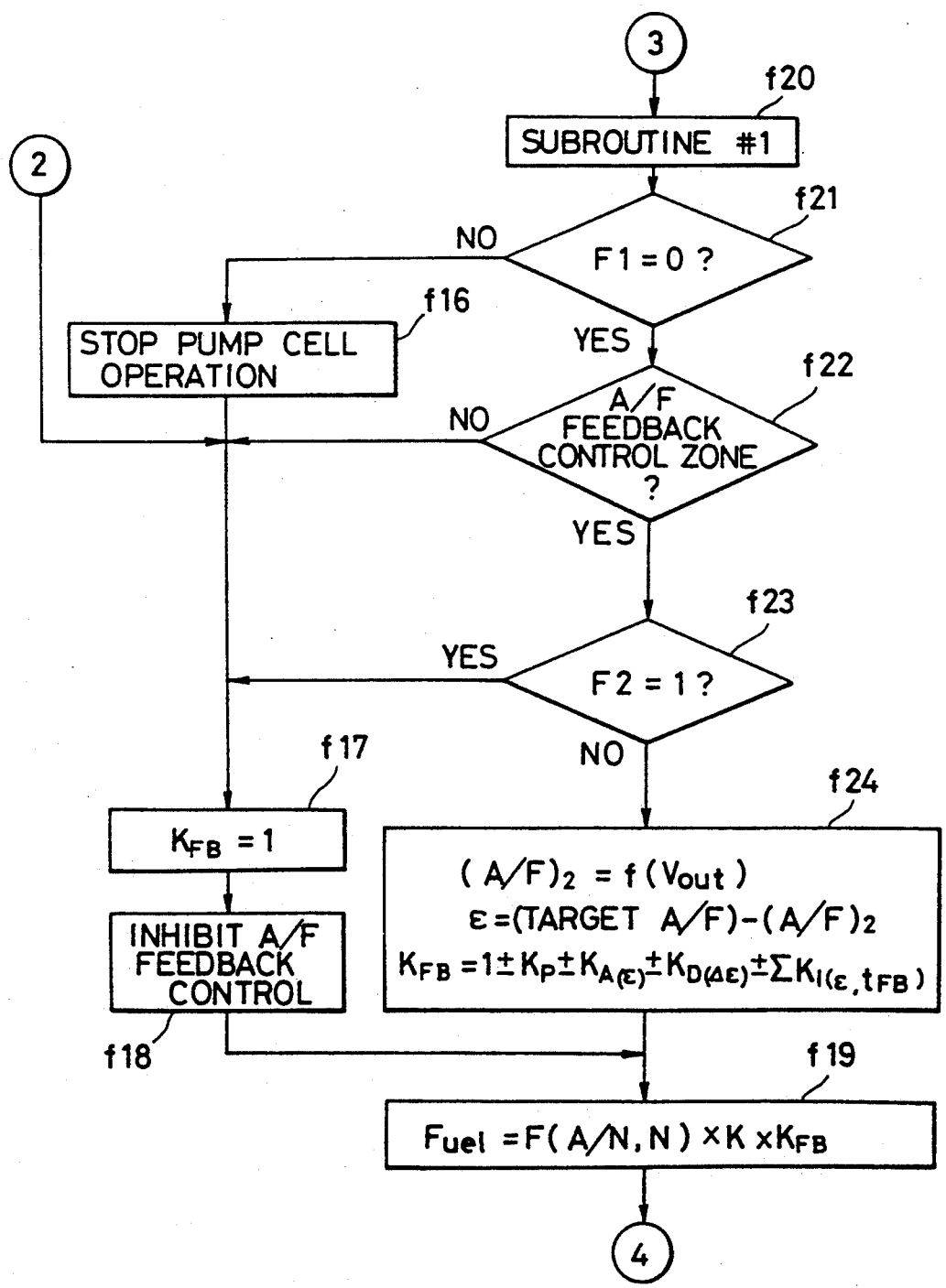
Figure 17:
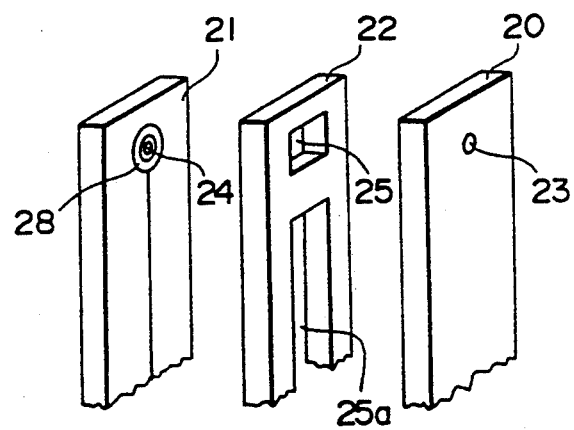
FIG. 17 is an exploded perspective view of a conventional air-fuel ratio sensor.

The controller 12 includes microcomputer, drivers 121 and 122, an input/output interface 123 for receiving various output signals and applying control signals to the drivers 121 and 122, a memory 124 which stores a control program for controlling the air-fuel ratio (see FIGS. 15(a) through 15(c)) and various threshold values, and a control unit 125 for calculating control values according to the control program.

The functions of the controller 12 will be described below with reference to FIG. 10. The controller 12 has a first unit including a deviation calculating portion responsive to an air-fuel ratio signal Vout from the control assembly 31 for the linear A/F sensor S, for calculating an error or difference $\Delta A/F$ between an actual air-fuel ratio according to the air-fuel ratio signal Vout and a target air-fuel ratio which is preset depending on operating conditions of the motor vehicle which incorporates the air-fuel ratio control system. The first unit also has a failure determining portion and a malfunction determining portion. The controller 12 also has a second unit including a malfunction processing portion and a failure processing portion, and an air-fuel ratio feedback control portion for effecting feedback control on the air-fuel ratio based on the air-fuel ratio signal.

The malfunction determining portion produces a malfunction signal if the error $\Delta A/F$ exceeds a threshold value $\pi$. The failure determining portion produces a failure signal if the error $\Delta A/F$ exceeds another threshold value $\alpha$. The malfunction processing portion interrupts the air-fuel ratio feedback control process based on the air-fuel ratio signal, when the malfunction signal is produced by the malfunction determining portion. The failure processing portion interrupts the air-fuel ratio feedback control process based on the air-fuel ratio signal and stops sensor operation, when the failure signal is produced by the failure determining portion.

Figure 13:
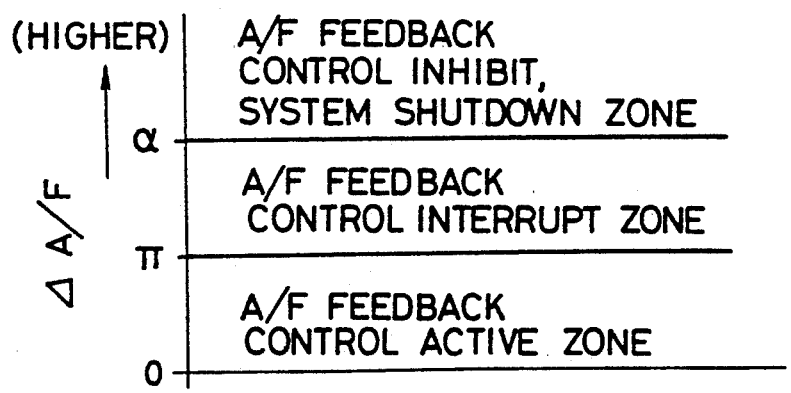
FIG. 13 is a diagram illustrative of various zones with respect to an air-fuel ratio difference in the air-fuel ratio control system shown in FIG. 11.

As shown in FIG. 13, the threshold value $\alpha$ is greater than the threshold value $\pi$.

Figure 14:
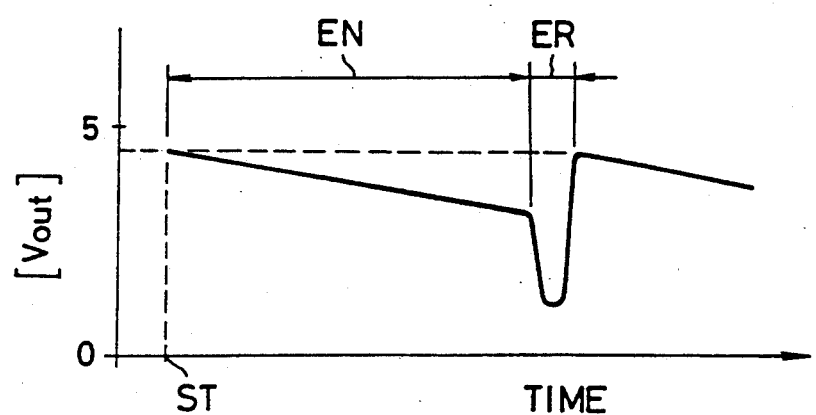
FIG. 14 is a diagram showing the output signal of a linear A/F sensor as it varies with time.

The threshold value $\pi$ is determined in view of a reduction in level of the air-fuel ratio signal Vout which takes place with time when the engine continuously operates with a lean air-fuel mixture (during an interval EN in FIG. 14). When the threshold value $\pi$ is exceeded, the air-fuel ratio feedback control process is interrupted, but the linear A/F sensor is allowed to operate. The other threshold value $\alpha$, which is greater than the threshold value $\pi$, is selected to be of such a level that if the error $\Delta A/F$ exceeds the threshold value $\alpha$, it is determined that the air-fuel sensor has failed and cannot be recovered from the failure.

A process of controlling an air-fuel, ratio with the air-fuel ratio control system shown in FIGS. 10 through 12 will be described with reference to the control program shown in FIGS. 15(a) through 15(c) and 16. The air-fuel ratio control process is carried out simultaneously with a process of controlling the rate of fuel to be injected (through air-fuel ratio feedback control and air-fuel ratio open-loop control) with the controller 37.

The control program has a main routine shown in FIGS. 15(a) and 15(b). In the main routine, the heater 30 (see FIG. 18) is turned on in a step f1, which is followed by a step f2 that determines whether a starter flag is 1 or not. If the starter flag is not 1, then control jumps to a step f8, and if the starter flag is 1, then control proceeds to a step f3. The starter flag is set when the starter switch SW is turned on, as shown in FIG. 15(c).

The starter flag is cleared to 0 in the step f3, and a fuel determining flag F1, and a malfunction flag F2, and a pump cell operation flag that allows the pump current Ip to be supplied are cleared in respective steps f4 and f5. In a step f6, a sensor starting timer is reset which defines a time to start the linear A/F sensor S. Thereafter, the sensor starting timer is started in a step f7.

A next step f8 determines whether the count of the sensor starting timer exceeds a preset value $\theta$ which has been set to an interval of time long enough for the air-fuel ratio sensor to be activated while the engine is being warmed up. If the count of the sensor starting timer does not exceed the preset value $\theta$, then control goes to a step f17 in which an air-fuel ratio feedback control coefficient KFB is set to 1. Then, the air-fuel ratio feedback control process is inhibited in a step f18. Subsequently control proceeds to a step f19 in which a fuel injection rate Fuel is calculated. Specifically, a rate of fuel to be injected is determined from a map depending on the engine rotational speed N and the engine load A/N, and the determined fuel injection rate Fuel is stored in a predetermined memory area. Stated otherwise, the open-loop process for controlling the rate of fuel to be injected is carried out in the step f19. Thereafter, control returns from the step f19 to the main routine. In a fuel injection routine (not shown) prior to the above process, the rate of fuel to be injected is determined in response to an interrupt at a certain crankshaft angle, and fuel is injected at the determined rate to achieve a target air-fuel ratio determined by the air-fuel ratio open-loop control process.

Thereafter, since the starter flag is 0 in the step f2, control goes from the step f2 directly to the step f8. If the count of the sensor starting timer exceeds the preset value $\theta$ in the step f8, then control proceeds to a step f9. In the step f9, if the sensor starting timer is still in operation, the counting operation thereof is stopped while retaining the count achieved so far. Then, control goes from the step f9 to a step f10.

The step f10 determines whether the pump cell operation flag is 1 or not. If the pump cell operation flag is not 1, then control proceeds to a step f11 in which the pump cell 21 is operated. Then, the pump cell operation flag is set to 1 in a step f12, which is followed by a step f13 in which a pump cell operation timer is started. A step f14 determines whether the count of the pump cell operation timer exceeds a preset value $\epsilon$ which has been set to an interval of time long enough for the output signal of the air-fuel ratio sensor to be stabilized. If the count of the pump cell operation timer does not exceed the preset value $\epsilon$, then control goes to the step f17 for continuing the open-loop control process. If the count of the pump cell operation timer exceeds the preset value $\epsilon$, i.e., if the sensor output becomes stable and the pump current Ip becomes reliable, then control goes from the step f14 to a step f15. In the step f15, if the pump cell operation timer is still in operation, the counting operation thereof is stopped while retaining the count achieved so far. Then, control goes from the step f15 to a step a20.

The step f20 determines whether the linear A/F sensor S has failed or not.

The step f20 is shown as a subroutine #1 in FIG. 16. The subroutine #1 determines whether the linear A/F sensor S has failed or not based on the air-fuel ratio signal Vout. If the fuel determining flag F1 is not 1 in a step g1 and the air-fuel ratio feedback control process is effected in a step g2, then control goes to a step g3. If the fuel determining flag F1 is 1 in the step g1 and the air-fuel ratio feedback control process is not effected in the step g2, then control returns to the main routine shown in FIGS. 15(a) and 15(b).

The step g3 reads a target air-fuel ratio that has already been determined in the main routine depending on operating conditions of the motor vehicle which incorporates the air-fuel ratio control system according to the present embodiment. Then, the air-fuel ratio signal Vout from the linear A/F sensor S is read in a step g4. A step g5 thereafter converts the air-fuel ratio signal Vout into an actual air-fuel ratio according to a predetermined map (not shown) of air-fuel ratios vs. air-fuel ratio signals.

A step g6 calculates a deviation or error $\Delta A/F$ between the target air-fuel ratio and the detected air-fuel ratio from the air-fuel ratio sensor. A step g7 then determines whether the error $\Delta A/F$ exceeds the threshold value $\alpha$ for determining a sensor failure or not. If the error $\Delta A/F$ does not exceed the threshold value $\alpha$, then control goes to a step g9. If the error $\Delta A/F$ exceeds the threshold value $\alpha$, then the fuel determining flag F1 is set to 1 in a step g8. Thereafter, control returns to the main routine. The step g9 determines whether the error $\Delta A/F$ exceeds the threshold value $\pi$ or not. If the error $\Delta A/F$ does not exceed the threshold value $\pi$, control returns to the main routine. If the error $\Delta A/F$ exceeds the threshold value $\pi$, then control goes to a step g10 in which the malfunction F2 is set. Thereafter, control returns to the main routine.

Back in the main routine, control goes to a step f21. The step f21 determines whether the fuel determining flag F1 is 0 or not. If the fuel determining flag F1 is not 0, it is determined that the error $\Delta A/F$ is in the A/F feedback control interrupt zone or the system shutdown zone. Control goes to a step f16 in which a pump cell operation stop signal is applied through the driver 122 to the pump current cutting circuit 14 to cut off the pump current Ip. Then, control proceeds from the step f16 to the step f17 for the air-fuel ratio open-loop control process.

If the fuel determining flag F1 is 0, then control proceeds from the step f21 to a step f22. The step f22 determines whether the present operating conditions of the motor vehicle fall, within an air-fuel ratio feedback control range or not. If the present operating conditions are not in the air-fuel ratio feedback control range, then control goes to the step f17 for the air-fuel ratio open-loop control process.

If the present operating conditions of the motor vehicle are in the air-fuel ratio feedback control range in the step f22, then control goes to a step f23. The step f23 determines whether the malfunction flag F2 is 1 or not. If the failure flag F2 is 1, then it is determined that the error $\Delta A/F$ is in the A/F feedback control interrupt zone, and control goes to the step f17 for the air-fuel ratio open-loop control process. If the malfunction flag F2 is zero in the step f23, then it is determined that the error $\Delta A/F$ is in the A/F feedback control active zone, and control goes to a step f24.

The step f24 calculates an actual air-fuel ratio $(A/F)_2$ based on the air-fuel ratio signal Vout according to the equation: $(A/F)_2 = f(Vout)$. Then, the target air-fuel ratio A/F that has already been determined in the main routine depending on operating conditions of the motor vehicle is read, and an error or difference $\epsilon$ between the read target air-fuel ratio A/F and the actual air-fuel ratio $(A/F)_2$ is calculated, and so is a difference $\Delta\epsilon$ between the presently calculated error $\epsilon$ and the previously calculated error. Finally in the step f24, a corrective coefficient $K_{FB}$ is calculated for the control of a fuel injection rate based on the air-fuel ratio.

The corrective coefficient $K_{FB}$ is calculated as the sum of, or difference between, a proportional term $K_{A(\epsilon)}$ of a gain depending on the level of the error $\epsilon$, an offset $K_p$ for the prevention of a response delay owing to the three-way catalytic converter, a differential term $K_{D(\Delta\epsilon)}$ depending on the difference $\Delta\Theta$, an integral term $\Sigma K_{I(\epsilon,tFB)}$, and 1.

Thereafter, control goes to the step f19 in which a proper rate of fuel to be supplied at the time is calculated from the corrective coefficients $K_{FB}$, K, and the basic fuel injection rate F(A/N,N). Control then returns to the step f1 in the main routine.

The rate of fuel to be supplied which is thus determined in the routine shown in FIGS. 15(a) and 15(b) is called in the fuel injection routine that is executed at the time of an interrupt effected in response to a crankshaft angle signal produced in the main routine. The fuel injection nozzle N is then actuated by the driver 121 for an interval of time corresponding to the determined rate of fuel to be supplied, thereby injecting fuel at the rate which achieves the desired air-fuel ratio.

Although certain preferred embodiments of the present invention have been shown and described in detail, it should be understood that various changes and modifications may be made therein without departing from the scope of the appended claims.

What is claimed is:

1. An air-fuel ratio control system for an internal combustion engine on a motor vehicle, comprising:
   an air-fuel ratio sensor for producing an air-fuel ratio signal indicative of the concentration of oxygen in an exhaust gas produced by a burned air-fuel mixture in the internal combustion engine;
   first means comprising failure determining means responsive to an output signal from said air-fuel ratio sensor and a target air-fuel ratio determined depending on operating conditions of the motor vehicle, for determining at least an irreparable failure of said air-fuel ratio sensor through comparison between said output signal and said target air-fuel ratio;
   air-fuel ratio feedback control means for correcting an air-fuel ratio correction according to at least said air-fuel ratio signal so that an actual air-fuel ratio of the internal combustion engine is equal to said target air-fuel ratio; and
   second means comprising failure processing means for disabling said air-fuel ratio feedback control means and said air-fuel ratio sensor in response to an output signal from said failure determining means which indicates an irreparable failure of said air-fuel ratio sensor.

2. An air-fuel ratio control system according to claim 1, wherein said first means further includes malfunction determining means responsive to the output signal from said air-fuel ratio sensor and the target air-fuel ratio, for determining a reparable malfunction of said air-fuel ratio sensor, and said second means further includes malfunction processing means for disabling said air-fuel ratio feedback control means in response to an output signal from said malfunction determining means which indicates a reparable malfunction of said air-fuel ratio sensor.

3. An air-fuel ratio control system according to claim 2, wherein said first means further includes error calculating means for calculating an error between said air-fuel ratio signal and said target air-fuel ratio, said failure determining means comprising means for comparing said error with a first preset value and determining a failure of said air-fuel ratio sensor when said error exceeds said first preset value, and said malfunction determining means comprising means for comparing said error with a second preset value smaller than said first preset value and determining a malfunction of said air-fuel ratio sensor when said error exceeds said second preset value.

4. An air-fuel ratio control system according to claim 1, wherein said air-fuel ratio sensor comprises a sensor cell for producing an output electric signal depending on the difference between the concentration of oxygen in the exhaust gas and the concentration of oxygen in a reference gas having an oxygen excess ratio which is sufficiently larger than 1, control means for detecting the output electric signal from said sensor cell and producing an electric control signal to cause said output electric signal to have a predetermined value, a pump cell for moving oxygen ions in response to the electric control signal from said control means, first detecting means for producing an air-fuel ratio signal depending on an electric current flowing between said control means and said pump cell, and second detecting means for producing a stoichiometric air-fuel ratio signal corresponding to a voltage developed across said pump cell, said failure determining means comprising means for comparing at least one of said air-fuel ratio signal and said stoichiometric air-fuel ratio signal with said target air-fuel ratio.

5. A method for controlling air-fuel ratio for an internal combustion engine on a motor vehicle, comprising the steps of:
(a) producing an air-fuel ratio signal by an air-fuel ratio sensor indicative of the concentration of oxygen in an exhaust gas produced by a burned air-fuel mixture in the internal combustion engine;
(b) comparing an output signal from said air-fuel ratio sensor and a target air-fuel ratio determined by operating conditions of the motor vehicle;
(c) determining at least an irreparable failure of said air-fuel ratio sensor through the comparison at said step (b);
(d) correcting an air-fuel ratio correction according to at least said air-fuel ratio signal so that an actual air-fuel ratio of the internal combustion engine is equal to said target air-fuel ratio; and
(e) disabling said air-fuel ratio correction at said step (d) and said air-fuel ratio sensor in response to an output signal from said step (c) which indicates an irreparable failure of said air-fuel ratio sensor.

6. A method for controlling air-fuel ratio according to claim 5, wherein said step (c) further includes the step of:
(c1) determining a reparable malfunction of said air-fuel ratio sensor and said target air-fuel ratio, and said step (e) further includes of the step of (e1) disabling said air-fuel ratio correction at said step (d) in response to an output signal from said step (c1) which indicates a reparable malfunction of said air-fuel ratio sensor.

7. A method for controlling air-fuel ratio according to claim 6, wherein said step (c) further includes the steps of:
(c2) calculating an error between said air-fuel ratio signal and said target air-fuel ratio,
(c3) comparing said error with a first preset value, and
(c4) determining a failure of said air-fuel ratio sensor when said error exceeds said first preset value, and said step (c1) further includes the steps of
(c5) comparing said error with a second preset value smaller than said first preset value, and
(c6) determining a malfunction of said air-fuel ratio sensor when said error exceeds said second preset value.

8. A method for controlling air-fuel ratio according to claim 5, wherein said step (a) further includes the step of:
(a1) producing an output electric signal by a sensor cell depending on a difference between a concentration of oxygen in the exhaust gas and a concentration of oxygen in a reference gas having an oxygen excess ratio which is sufficiently larger than 1,
(a2) detecting said output electric signal from said sensor cell,
(a3) producing an electric control signal by control means to cause said output electric signal to have a predetermined value,
(a4) moving oxygen ions by a pump cell in response to said electric control signal produced at said step (a3),
(a5) producing an air-fuel ratio signal depending on an electric current flowing between said control means and said pump cell, and
(a6) producing a stoichiometric air-fuel ratio signal corresponding to a voltage developed across said pump cell, and
said step (c) further includes the step of comparing at least one said air-fuel ratio signal and said stoichiometric air-fuel ratio signal with said target air-fuel ratio.

9. A method for controlling air-fuel ratio for an internal combustion engine on a motor vehicle, comprising the steps of:
(a) producing an air-fuel ratio signal by an air-fuel ratio sensor in proportion to a concentration of oxygen in an exhaust gas produced by a burned air-fuel mixture in the internal combustion engine;
(b) producing an output electric signal by a sensor cell depending on a difference between a concentration of oxygen in a reference gas having an oxygen excess ratio which is larger than 1;
(c) detecting said output signal produced at said step (b) from said sensor cell;
(d) producing an electric control signal by control means to cause said output electric signal to have a predetermined value;
(e) moving oxygen ions by a pump cell in response to said electric control signal produced at said step (d);
(f) producing an air-fuel ratio signal depending on an electric current flowing between said control means and said pump cell;
(g) producing a stoichiometric air-fuel ratio signal corresponding to a voltage developed across said pump cell; and (h) determining at least an irreparable failure of said air-fuel ratio sensor through a comparison between an output signal from said air-fuel ratio sensor and a target air-fuel ratio determined depending on operating conditions of the motor vehicle, the comparison including the step of comparing at least one said air-fuel ratio signal and said stoichiometric air-fuel ratio signal with said target air-fuel ratio.

10. A method for controlling air-fuel ratio according to claim 9, further including the step (i) determining a reparable malfunction of said air-fuel ratio sensor responsive to the output signal from said air-fuel ratio sensor and said target air-fuel ratio.

11. A method for controlling air-fuel ratio according to claim 10, further including the step of:
 (j) calculating an error between said air-fuel ratio signal and said target air-fuel ratio,
 (k) comparing said error with a first preset value,
 (l) determining a failure of said air-fuel ratio sensor when said error exceeds said first preset value,
 (m) comparing said error with a second preset value smaller than said first preset value, and
 (n) determining a malfunction of said air-fuel ratio sensor when said error exceeds said second preset value.

* * * * *